(12) United States Patent
Kramer et al.

(10) Patent No.: US 7,585,806 B2
(45) Date of Patent: Sep. 8, 2009

(54) CATALYST COMPOSITIONS AND PROCESS FOR OXYCHLORINATION

(75) Inventors: Keith S. Kramer, Avon Lake, OH (US); Joseph A. Cowfer, Avon Lake, OH (US)

(73) Assignee: Oxy Vinyls, LP, Dallas, TX (US)

( * ) Notice: Subject to any disclaimer, the term of this patent is extended or adjusted under 35 U.S.C. 154(b) by 7 days.

(21) Appl. No.: 11/558,449

(22) Filed: Nov. 10, 2006

(65) Prior Publication Data

US 2007/0112235 A1 May 17, 2007

Related U.S. Application Data

(60) Provisional application No. 60/736,524, filed on Nov. 14, 2005.

(51) Int. Cl.
*B01J 21/08* (2006.01)
*C03C 10/10* (2006.01)

(52) U.S. Cl. .................. 502/240; 502/243; 502/244; 501/6

(58) Field of Classification Search ............... 558/208; 570/243; 502/300, 240, 243, 244; 501/6
See application file for complete search history.

(56) References Cited

U.S. PATENT DOCUMENTS

| | | | |
|---|---|---|---|
| 3,992,463 A | 11/1976 | Benaroya et al. | |
| 4,029,616 A | 6/1977 | Nakashio et al. | |
| 4,226,798 A | 10/1980 | Cowfer et al. | |
| 4,246,039 A | 1/1981 | Mixon | |
| 4,339,620 A | 7/1982 | Cowfer et al. | |
| 4,341,634 A | 7/1982 | Matsushita et al. | |
| 4,388,278 A | 6/1983 | Schmidhammer et al. | |
| 4,409,394 A | 10/1983 | Vangermain et al. | |
| 4,427,450 A | 1/1984 | Kostansek | |
| 4,446,249 A | 5/1984 | Eden | |
| 4,493,902 A | 1/1985 | Brown et al. | |
| 4,525,518 A | 6/1985 | Kostansek | |
| 4,578,118 A | 3/1986 | Huege et al. | |
| 4,590,325 A | 5/1986 | Imai et al. | |
| 4,678,517 A | 7/1987 | Dunaway | |
| 4,740,642 A | 4/1988 | Eden et al. | |
| 4,754,088 A | 6/1988 | Schmidhammer et al. | |
| 4,788,358 A | 11/1988 | Riedl et al. | |
| 4,820,550 A | 4/1989 | Noaki et al. | |
| 4,849,393 A * | 7/1989 | Eden et al. ............... 502/225 |
| 4,917,988 A | 4/1990 | Koizumi et al. | |
| 5,006,574 A | 4/1991 | Sennett et al. | |
| 5,011,534 A | 4/1991 | Berube et al. | |
| 5,023,220 A | 6/1991 | Dight et al. | |
| 5,028,268 A | 7/1991 | Ince et al. | |
| 5,039,821 A | 8/1991 | Mathiaparanam | |
| 5,061,461 A | 10/1991 | Sennett et al. | |
| 5,074,475 A | 12/1991 | Suitch et al. | |
| 5,112,782 A | 5/1992 | Brown et al. | |
| 5,116,799 A * | 5/1992 | Correia et al. ............... 502/225 |
| 5,129,953 A | 7/1992 | Suitch et al. | |
| 5,202,511 A * | 4/1993 | Salinas et al. ............... 570/245 |
| 5,261,956 A | 11/1993 | Dunaway et al. | |
| 5,292,703 A | 3/1994 | Young et al. | |
| 5,382,726 A | 1/1995 | Young et al. | |
| 5,393,340 A | 2/1995 | Slepetys et al. | |
| 5,478,867 A | 12/1995 | Tabor | |
| 5,522,924 A | 6/1996 | Smith et al. | |
| 5,600,043 A | 2/1997 | Johnston et al. | |
| 5,648,508 A | 7/1997 | Yaghi | |
| 5,733,572 A | 3/1998 | Unger et al. | |
| 5,741,869 A | 4/1998 | Goodall et al. | |
| 5,856,397 A | 1/1999 | Pope et al. | |
| 5,968,250 A | 10/1999 | Sheppard et al. | |
| 5,972,827 A | 10/1999 | Petit et al. | |
| 5,997,626 A | 12/1999 | Wu et al. | |
| 6,103,005 A | 8/2000 | Sare et al. | |
| 6,136,086 A | 10/2000 | Hen et al. | |
| 6,180,841 B1 | 1/2001 | Fatutto et al. | |
| 6,346,145 B1 | 2/2002 | Hen et al. | |
| 6,379,452 B1 | 4/2002 | Maxwell et al. | |
| 6,452,059 B1 | 9/2002 | Casagrande et al. | |
| 6,585,822 B2 | 7/2003 | Berube et al. | |
| 6,593,269 B1 * | 7/2003 | Rubini et al. ............... 502/225 |
| 6,652,642 B2 | 11/2003 | Sare et al. | |
| 6,680,415 B1 * | 1/2004 | Gulotty et al. ............... 570/243 |
| 6,680,416 B1 | 1/2004 | Hebgen et al. | |
| 6,740,373 B1 | 5/2004 | Swoboda et al. | |
| 6,759,365 B2 | 7/2004 | Cavalli et al. | |
| 6,777,373 B1 | 8/2004 | Carmello et al. | |
| 6,797,845 B1 | 9/2004 | Hickman et al. | |
| 6,872,684 B2 | 3/2005 | Casagrande et al. | |

(Continued)

FOREIGN PATENT DOCUMENTS

EP 0060317 9/1982

(Continued)

OTHER PUBLICATIONS

Zeolites definition—from NPL: Wikipidea.*

(Continued)

*Primary Examiner*—Jafar Parsa
(74) *Attorney, Agent, or Firm*—Jones Day; Benjamin Bai; Kam W. Law

(57) ABSTRACT

Oxychlorination catalyst compositions which include a catalytically effective amount of an oxychlorination catalyst and a diluent having certain chemical composition and/or physical properties are disclosed. Processes using such oxychlorination catalyst compositions are also described. Some oxychlorination catalyst compositions and processes disclosed herein can increase the optimal operating temperature, and thereby increase the production capacity of an existing reactor, such as a fluid-bed reactor, compared to other oxychlorination catalyst compositions.

24 Claims, 8 Drawing Sheets

U.S. PATENT DOCUMENTS 6,942,784 B2 9/2005 Stockwell et al.
6,943,132 B2 9/2005 Stockwell et al.
7,126,035 B2 * 10/2006 Kuhrs et al. .................. 570/203

FOREIGN PATENT DOCUMENTS

| EP | 0060317 | A1 | 9/1982 |
| EP | 00660317 | A1 | 9/1982 |
| EP | 1020222 | A2 | 7/2000 |
| GB | 1190942 | | 5/1970 |
| GB | 1190942 | A | 5/1970 |
| GB | 1474258 | * | 5/1977 |
| JP | 11-292803 | A | 10/1999 |
| JP | 11-292804 | A | 10/1999 |
| JP | 11-292805 | A | 10/1999 |
| WO | WO 9850328 | | 11/1998 |

OTHER PUBLICATIONS

Maintain High Activity and Attrition Resistance in USY Octane Catalysts, downloaded at http://www.refiningonline.com/EngelhardKB/crep/TCR4_25.htm on Jan. 23, 2007.
Shuqin Zheng et al., Effect of Properties of Calcined Microspheres of kaolin on the Formation of NaY Zeolite, Bulletin of the Catalysis Society of India, 4 (2005)12-17.
ISR of corresp. PCT ap., Arp. 11, 2007.
PCT Search report, Apr. 11, 2007.

* cited by examiner

CATALYST COMPOSITIONS AND PROCESS FOR OXYCHLORINATION

PRIOR RELATED APPLICATIONS

This application claims priority to U.S. Provisional Patent Application Ser. No. 60/736,524, filed Nov. 14, 2005, which is incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to oxychlorination catalyst compositions for catalytically oxychlorinating hydrocarbons to chlorinated hydrocarbons, especially compositions comprising an oxychlorination catalyst and a diluent and their applications in oxychlorination processes.

BACKGROUND OF THE INVENTION

Oxychlorination catalyst compositions for the production of chlorinated hydrocarbons by oxychlorination have been well established for many years. Oxychlorination is the reaction of a hydrocarbon, such as ethylene or propylene, with hydrogen chloride and oxygen to form water and the corresponding chlorinated hydrocarbons, such as 1,2-dichloroethane (EDC) or 1,2-dichloropropane, preferably in the presence of an oxychlorination catalyst. The oxychlorination reaction has been applied worldwide in large industrial scale. For example, the conversion of ethylene to EDC by oxychlorination alone is currently in a scale of million's of tons per year.

One particular method of oxychlorination is the vapor phase reaction of a hydrocarbon, such as ethylene or propylene, with a mixture of hydrogen chloride (HCl) and a source of oxygen (such as high purity oxygen obtained from an air separation plant where pressure swing absorption or cryogenic separation is employed to remove inert materials, or a dilute oxygen stream such as air or a mixture of oxygen and at least an inert gas) within a fluidized catalyst bed comprising an oxychlorination catalyst. A typical oxychlorination catalyst can comprise a metal salt such as copper chloride and optionally at least a salt of alkali metals, alkaline metals or rare earth metals deposited on or combined with a support material or inert carrier, such as particles of silica, alumina, kieselguhr, fuller's earth, clays and alumina silicates or aluminum silicates or aluminium silicates. For use in fluid-bed catalysis, the support material should be readily fluidizable having the proper particle density, resistance to attrition, and particle size distribution to be useful in the process without generating excessive catalyst loss from the reaction zone. Optionally, the catalyst composition may comprise a diluent which comprises catalytically and chemically inert particles such as alumina and silica having a low surface area.

In the oxychlorination of a hydrocarbon (e.g., ethylene), it is desirable for the oxychlorination catalyst composition to effect a high yield of the desired chlorinated product (e.g., EDC) and a small amount of by-products such as carbon dioxide, carbon monoxide and other chlorinated materials. In the high volume business of manufacturing EDC, a small increase in the efficiency of ethylene conversion to EDC can provide significant cost savings. Furthermore, an increase in ethylene efficiency or selectivity of ethylene to EDC can reduce the amount of by-products produced, the associated costs to dispose of them properly, and the potential risks to the environment. Selectivity of ethylene to EDC (i.e., ethylene selectivity) is the number of moles of pure EDC produced per 100 moles of ethylene consumed or converted (i.e., ethylene conversion) to EDC plus any by-products, whereas ethylene efficiency is defined as the product of ethylene selectivity times ethylene conversion. Similarly, selectivity of HCl to EDC (i.e., HCl selectivity) is the number of moles of pure EDC produced per 200 moles of HCl consumed or converted (i.e., HCl conversion) to EDC plus any by-products, whereas HCl efficiency is defined as the product of HCl selectivity times HCl conversion. Similarly, selectivity of oxygen to EDC (i.e., oxygen selectivity) is the number of moles of pure EDC produced per 50 moles of oxygen consumed or converted (i.e., oxygen conversion) to EDC plus any by-products, whereas oxygen efficiency is defined as the product of oxygen selectivity times oxygen conversion.

It is also desirable, for economic and environmental reasons, for the oxychlorination catalyst composition to effect a high conversion of HCl used in the reaction. Unconverted HCl needs to be neutralized by a base and the resulting salt must be disposed. Also, high levels of unconverted HCl in the process generally leads to high HCl "break through" downstream in the reactor which can cause corrosion problems. Hence, it is desirable to operate a reactor at an optimal temperature to provide high HCl conversion. In commercial applications, a combination of high HCl conversion and high ethylene efficiency or selectivity of ethylene to EDC is most desirable.

Further, it is desirable to increase the optimal operating temperature of the oxychlorination catalyst without sacrificing catalyst performance because it would be the most cost efficient way to increase the production capacity of an existing oxychlorination reactor. In general, an increase in the operating temperatures increases the temperature difference between the fluidized catalyst bed and the steam drum, which is utilized for removing the heat of reaction and maintaining the controlled temperature. Therefore, increasing the operating temperature can increase the driving force for heat removal and allow for increased reactor productivity. The optimal operating temperature for the catalyst in reactors where the majority of the vent gas is recycled back to the reactor is the point where the HCl conversion and the ethylene selectivity are optimized. For air-based, once-through reactors, the optimal operating temperature is the point where the HCl conversion and the ethylene efficiency are optimized. For example, for a reactor limited by a steam drum pressure of 211 psig (i.e., 1455 kPa) and/or 200° C., an increase in the optimal operating temperature of the oxychlorination catalyst composition from 230° C. to 240° C. would result in an increase of 33% in the production capacity of that reactor. Therefore, there is always a need for oxychlorination catalyst compositions that can run at higher optimal operating temperatures thus providing an effective way to increase the production capacity of an existing oxychlorination reactor.

SUMMARY OF THE INVENTION

Disclosed herein are oxychlorination catalyst compositions that can increase the optimal operating temperature of oxychlorination processes without sacrificing catalyst performance.

In one aspect, the oxychlorination catalyst compositions comprise a catalytically effective amount of an oxychlorination catalyst and a diluent comprising particles of an alumina silicate.

In another aspect, the oxychlorination catalyst compositions comprise:

(a) a catalytically effective amount of an oxychlorination catalyst having a surface area greater than 25 m²/g where the oxychlorination catalyst comprises a support material having distributed thereon an active salt composition; and (b) a diluent having a surface area between about 0.1 m²/g and about 25 m²/g, wherein the support material and the diluent are different chemically and the average particle size of the catalyst and the diluent is between about 5 and about 300 microns.

Disclosed herein are also oxychlorination processes using the oxychlorination catalyst compositions to increase the optimal operating temperature of the oxychlorination processes without sacrificing catalyst performance.

In one aspect, the oxychlorination processes comprise the step of contacting reactants including the hydrocarbon, a source of chlorine, and an oxygen source with an oxychlorination catalyst composition under process conditions to prepare a chlorinated hydrocarbon. In some embodiments, the oxychlorination catalyst composition comprises a catalytically effective amount of an oxychlorination catalyst and a diluent comprising particles of an alumina silicate. In other embodiments, the oxychlorination catalyst composition comprises (a) a catalytically effective amount of an oxychlorination catalyst having a surface area greater than 25 m²/g where the oxychlorination catalyst comprises a support material having distributed thereon an active salt composition; and (b) a diluent having a surface area between about 0.1 m²/g and about 25 m²/g, wherein the support material and the diluent are different chemically and the average particle size of the catalyst and the diluent is between about 5 and about 300 microns.

In another aspect, the oxychlorination processes comprise the step of contacting reactants including the hydrocarbon, a source of chlorine, and an oxygen source with an oxychlorination catalyst composition comprising a catalytically effective amount of an oxychlorination catalyst and an inert diluent under process conditions to prepare a chlorinated hydrocarbon, wherein the process is run at $T_{opt(2)}$, the optimal operating temperature of the process, which is at least about 1° C. higher than $T_{opt(1)}$, the optimal operating temperature of a process using the same reactor, reactants, production rates and oxychlorination catalyst but without the inert diluent. In some embodiments, the oxychlorination processes are operated at the most economical process conditions.

DETAILED DESCRIPTION OF THE INVENTION

Figure 1:
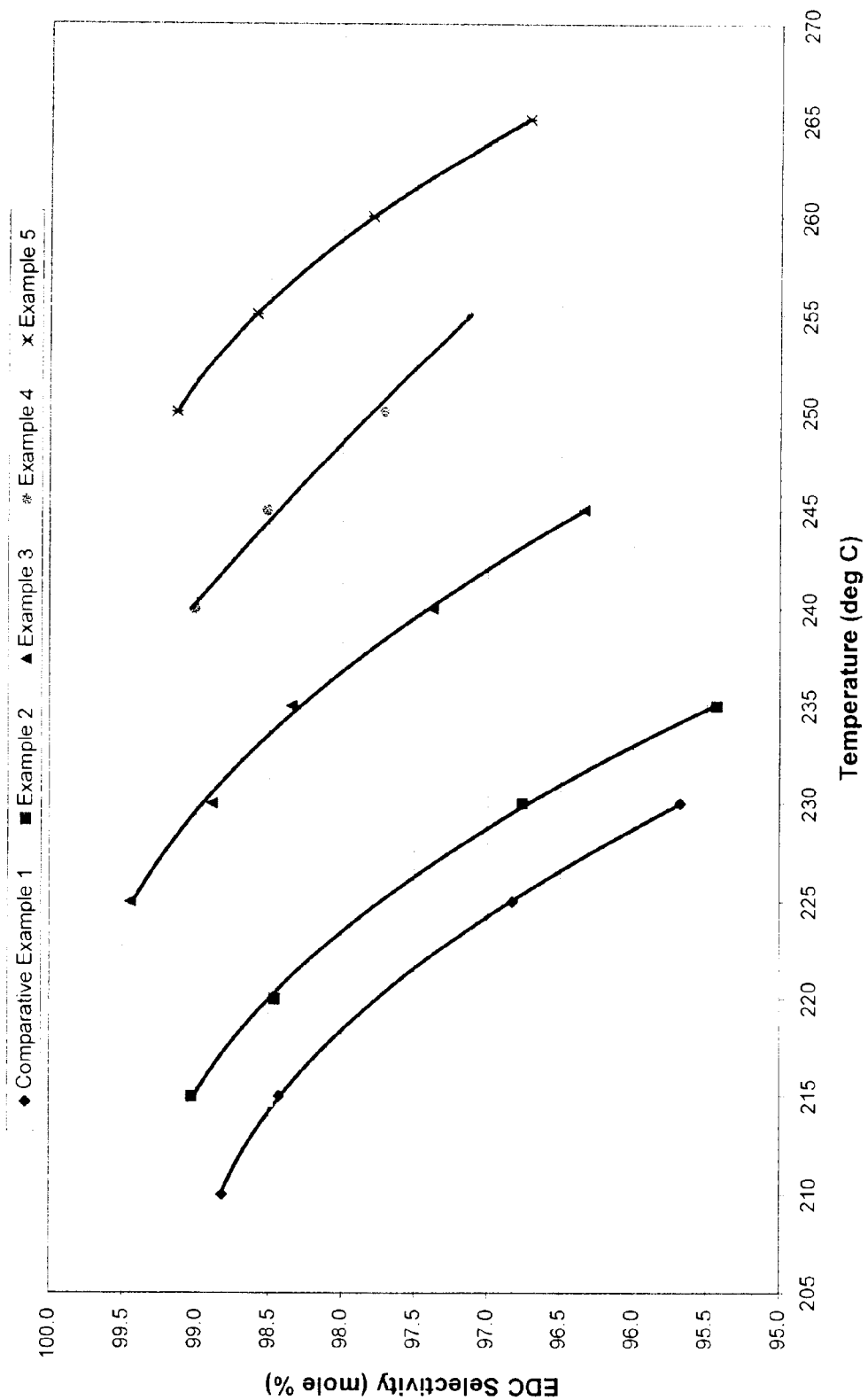
FIG. 1 depicts the EDC selectivity as a function of temperature and catalyst composition of Examples 1-5 disclosed herein.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

This invention provides an oxychlorination catalyst composition comprising a catalytically effective amount of an oxychlorination catalyst and a diluent such as alumina silicates (also known as aluminum silicates or aluminium silicates), glass beads, silica, ballotini, alumina, graphite, and silicon carbide. The oxychlorination catalyst composition can provide a higher optimal operating temperature without sacrificing the performance benefits inherent to the undiluted oxychlorination catalyst such as high EDC selectivity, high product purity, high HCl conversion, and excellent fluidity. As used herein, the term "catalytically effective amount" is intended to mean any amount that is effective in generating an EDC production capacity increase of the oxychlorination reactor by at least 1%, preferably by at least 10%, more preferably by at least 30%, and most preferably by at least 50%.

In some embodiments, the oxychlorination catalyst composition comprises from about 10 to about 90 percent by weight of the oxychlorination catalyst and from about 90 to about 10 percent by weight of the diluent. In other embodiments, the oxychlorination catalyst composition comprises from about 20 to about 80 percent by weight of the oxychlorination catalyst and from about 80 to about 20 percent by weight of the diluent. In further embodiments, the oxychlorination catalyst composition comprises from about 30 to about 70 percent by weight of the oxychlorination catalyst and from about 70 to about 30 percent by weight of the diluent. In particular embodiments, the oxychlorination catalyst composition comprises from about 60 to about 40 percent by weight of the oxychlorination catalyst and from about 60 to about 40 percent by weight of the diluent.

Some oxychlorination catalyst compositions described herein can be characterized by an ethylene to EDC selectivity of at least 96% at a temperature of 230° C. Other oxychlorination catalyst compositions can be characterized by an ethylene to EDC selectivity of at least 97% at a temperature of 240° C. Some oxychlorination catalyst compositions can be characterized by substantially the same or higher ethylene to EDC selectivity, HCl conversion and/or higher operating temperatures than a comparable oxychlorination catalyst without a diluent having a surface area of less than 25 m$^2$/g.

The oxychlorination catalyst can be any oxychlorination catalyst known to one of ordinary skill in the art. It can also be prepared by any method known to one of ordinary skill in the art. The oxychlorination catalyst can contain an active salt composition comprising a copper salt such as copper chloride distributed, coated, deposited or supported on a support material. The active salt composition may also contain an active metal oxide or metal salt that is co-precipitated with the support. Alternatively, the active salt composition can be unsupported, but fused into a molten salt. In some embodiments, the active salt composition further comprises at least one metal salt or oxide derived from a metal selected from the group consisting of alkali metals, alkaline metals (i.e., Group IIA), rare earth metals and combinations thereof. The anion of the metal salt can be any anion known in the art such as chloride, bromide, iodide, nitrate, bicarbonate, carbonate and carboxylates (e.g., formate and acetate). In some embodiments, the active salt composition comprises a copper salt, at least one alkali metal salt, at least one rare earth metal salt, and at least one alkaline metal salt. In other embodiments, the active salt composition does not contain an alkali metal salt, an alkaline metal salt, a rare earth metal salt, or a transition metal salt other than a copper salt. Some non-limiting examples of suitable oxychlorination catalysts, active salt compositions and support materials are disclosed in PCT Patent Application No. WO 81/01284, U.S. Pat. Nos. 3,488,398; 4,339,620; 4,446,249; 4,740,642; 4,849,393; 5,292,703; 5,382,726; 5,600,043; 6,872,684; 6,803,342; 6,777,373; 6,759,365; and 6,174,834, and Japanese Patent Publication No. 11-090233, all of which are incorporated herein by reference in their entirety.

The average particle size and the particle size distribution of the oxychlorination catalyst, the support material, or the diluent can be measured with a particle size analyzer. As used or claimed herein, the average particle size and the particle size distribution data are or should be measured by ASTM D4460-00, which is incorporated herein by reference or by the procedure described below. The average particle size and the particle size distribution can be measured with a Honeywell Microtrac X-100 laser particle analyzer using water as the dispersant. The samples for the measurement can be prepared by adding about 5 ml of the particles to 10 ml of a surfactant solution (which is prepared from 4 ml of TRITON™ CF-10 (from Rohm and Haas Company, Philadelphia, Pa.) and 6 ml of TRITON™ X-100 (from Rohm and Haas Company, Philadelphia, Pa) diluted with water to 1000 ml) in a 50 ml beaker. The mixture is stirred to wet all particles for about 10 to 15 seconds to generate a slurry that is then added to the circulator basin of the Microtrac X-100 containing about 2 liters of water. Once the proper concentration level is confirmed by the software (about 10 to 20 seconds), the run is initiated. The water temperature is held between about 80 and 90° F. The Microtrac X-100 particle size analyzer utilizes the laser diffraction method to measure the percent of particles in the range of 0.04 to 700 microns. The average particle size is the 50% point (by volume) of the sample. The particle size distribution is reported as percentages of particles less than some particular size in microns. Alternatively, the average particle size and the particle size distribution of the samples can be measured by an equivalent instrument or method that produces essentially the same results obtained by the Honeywell Microtrac X-100 laser particle analyzer.

A person of ordinary skill in the art can recognize that the measurements of the average particle size and the particle size distribution may be subject to errors and/or variations, depending on many factors such as the type of the particle analyzer used for the measurement, the calculation method including error correction algorithm, the sample preparation method, the amount and nature of the dispersant, the amount and nature of the surfactant and the like. For the oxychlorination catalyst compositions disclosed herein, the relative values of the average particle sizes and the particle size distributions of the oxychlorination catalyst, the support material and the diluent are as significant as their absolute values. The relative values of the average particle sizes and the particle size distributions of the oxychlorination catalyst, the support material and the diluent can be measured by any particle size measurement method known to a skilled artisan. For example, the relative average particle size of the diluent or the support material to the average particle size of the oxychlorination catalyst can be obtained by ASTM D4460-00 or the method described above or any similar method known to a person skilled in the art.

The surface area of the support material, the oxychlorination catalyst or the diluent can be determined by the BET (Brunauer-Emmet-Teller) method of measuring surface area, as described by S. Brunauer, P. H. Emmett, and E. Teller, Journal of the American Chemical Society, 60, 309 (1938), which is incorporated herein by reference. As used or claimed herein, the surface area data are or should be calculated from the nitrogen adsorption isotherm data at 77° K utilizing the BET method. The support material, the oxychlorination catalyst or the diluent can have either a high surface area or a low surface area. As used herein, the term "high surface area" or "high-surface-area" means a surface area greater than 25 m$^2$/g, preferably greater than about 50 m$^2$/g, more preferably greater than about 70 m$^2$/g. Further, as used herein, the term "low surface area" or "low-surface-area" means a surface area less than 25 m$^2$/g, preferably less than about 20 m$^2$/g, more preferably less than about 16 m$^2$/g.

Any support material which is known in the art suitable as a support for oxychlorination catalyst can be used in this invention. Non-limiting examples of suitable support materials include alumina such as activated alumina and microgel alumina, silica, magnesia, kieselguhr, fuller's earth, clays, alumina silicates, porous rare earth halides and oxyhalides, and combinations thereof. The support material can have a surface area between about 5 m$^2$/g and about 450 m$^2$/g, as determined by the BET method. In some embodiments, the surface area of the support material is between about 25 m$^2$/g and about 300 m$^2$/g. In further embodiments, the surface area of the support material is between about 70 m$^2$/g and about 200 m$^2$/g. In certain embodiments, the surface area of the support material is between about 70 m$^2$/g and about 240 m$^2$/g.

The support material can have an average particle size ranging from about 5 to about 300 microns, from about 20 to about 250 microns, from about 20 to about 200 microns, from about 20 to about 150 microns, from about 20 to about 120 microns, from about 30 to about 100 microns, or from about 30 to about 90 microns. The compacted or tamped bulk density of the support material can vary between about 0.6 and about 1.6 g/cc, between about 0.7 and about 1.5 g/cc, between about 0.7 and about 1.3 g/cc, or between about 0.8 and about 1.3 g/cc.

In fluid-bed oxychlorination catalysis, it is desirable that the support materials have a high surface area because high-surface-area support materials can reduce the tendency for stickiness of the oxychlorination catalyst as the active salt composition is dispersed over a large area. Catalyst stickiness is defined as catalyst particle agglomeration via copper chloride mobility and bridging from particle to particle under process operating conditions. In fixed-bed catalysis, the support material can have either a high surface area or a low surface area. The preferred catalytic process is fluid-bed catalysis using a high-surface-area support material.

The oxychlorination catalyst used for the fluid-bed catalysis process can comprise an active salt or oxide composition uniformly distributed, deposited, coated, co-precipitated with, or supported on a high-surface-area support material. The support material can be in the form of particles having proper particle sizes, surface area, porosity, density, resistance to attrition and other characteristics (a) to provide uniform fluidization, good heat transfer, and minimal temperature gradients in the reactor bed; (b) to permit adequate contact between the active salt composition and the gaseous reactants as they pass through the bed; and (c) to minimize loss of catalyst through passage of fine particles from the reactor with the effluent gases.

In some embodiments, the support material having a surface area greater than 50 $m^2/g$ and the support material is selected from the group consisting of alumina silicate, silica, alumina, and combinations thereof. In a particular embodiment, the support materials are aluminas having a surface area in the range of about 25 to 250 $m^2/g$, a compacted bulk density in the range of 0.7 to 1.1 g/cc, and an average particle size ranging from about 5 to about 300 microns. Such alumina support materials are readily fluidizable, relatively stable, mechanically strong and resistant to attrition. In some embodiments, the support material is an alumina having a surface area in the range of about 120 to 240 $m^2/g$ and an average particle size ranging from about 30 to about 90 microns.

It is recognized that some alumina support materials may contain, in addition to aluminum oxide ($Al_2O_3$), small amounts of other metal compounds such as metal oxides. Non-limiting examples of metal oxides in aluminum oxide include sodium oxide, magnesium oxide, titanium oxide and the like. These alumina support materials are readily useable in this invention. Similarly, some alumina silicate support materials may contain in addition to alumina silicate small amounts of other metal compounds such as metal silicates and metal oxides. Non-limiting examples of metal oxides in alumina silicate include sodium oxide, magnesium oxide, iron oxide, and the like. These alumina silicate support materials are also readily useable in this invention. The other metal compounds may occur naturally or be added as separate compounds.

In some embodiments, the active salt composition comprises a copper salt. The copper salt can be used in the form of a water soluble salt, preferably copper chloride. However, copper oxides or other copper salts, such as the nitrate salt, carbonate salt and other halide salts like the bromide salt, that could convert to the chloride during the oxychlorination process can also be used. The amounts of copper salt and other salts in the oxychlorination catalyst depend on the activity desired and the specific fluidization characteristics of the support material for fluid-bed catalyst applications. The amount of copper metal content can be in the range from about 1% by weight to about 15% by weight, based on the total weight of the oxychlorination catalyst. In some embodiments, the amount of copper metal content is about 2% by weight to about 8% by weight, based on the total weight of the oxychlorination catalyst. In other embodiments, the amount of copper metal in the copper salt is in the range from about 3% to about 6% by weight based on the total weight of the oxychlorination catalyst. In other embodiments, the amount of copper metal in the copper salt is in the range from about 7% to about 12% by weight based on the total weight of the oxychlorination catalyst.

The active salt composition can also comprise an alkali metal salt or oxide. The alkali metal of the alkali metal salts employed in the present invention can be selected from the group consisting of sodium, potassium, lithium, rubidium, cesium, and mixtures thereof. The alkali metal salt can be in the form of a water soluble salt, such as an alkali metal chloride. However, other alkali metal salts or oxides that would convert to the chloride salts during the oxychlorination process can also be used, such as the carbonate salts and other halide salts like the bromide salts. In some embodiments, the alkali metal is potassium, lithium, or cesium. In another embodiment, the alkali metal is potassium. In one particular embodiment, the alkali metal salt is potassium chloride. The amount of the alkali metal in the alkali metal salt can be in the range from about 0.1% to about 8.0% by weight based on the total weight of the oxychlorination catalyst. In some embodiments, the amount of the alkali metal in the alkali metal salt is in the range from about 0.25% to about 5% by weight based on the total weight of the oxychlorination catalyst. In other embodiments, the amount of the alkali metal in the alkali metal salt is in the range from about 0.5% to about 2.5% by weight based on the total weight of the oxychlorination catalyst.

In some embodiments, the active salt composition comprises a rare earth metal salt or oxide. The rare earth metal in the rare earth metal salts used herein can be any of the elements listed as elements 57 through 71 in the Periodic Table and the pseudo rare earth elements yttrium and scandium. Non-limiting examples of the rare earth metals include lanthanum, cerium, neodymium, praseodymium, dysprosium, samarium, yttrium, gadolinium, erbium, ytterbium, holmium, terbium, europium, thulium, lutetium, and mixtures thereof such as didymium which is a mixture of praseodymium and neodymium. The preferred rare earth metal salts are rare earth metal chlorides. However, other rare earth metal salts or oxides which would convert into the chloride salts during the oxychlorination process can also be used, e.g., carbonate salts, nitrate salts and other halide salts like bromide salts. The amount of the rare earth metal in the rare earth metal salts can be in the range from about 0.1% to about 9% by weight based on the total weight of the oxychlorination catalyst. In some embodiments, the amount of the rare earth metal in the rare earth metal salt is in the range from about 0.5% to about 6% by weight based on the total weight of the oxychlorination catalyst. In other embodiments, the amount of the rare earth metal in the rare earth metal salt is in the range from about 0.5% to about 3% by weight based on the total weight of the oxychlorination catalyst. In other embodiments, the rare earth metal salt is cerium chloride or didymium chloride. In some embodiments, the rare earth metal salt is a mixture of lanthanum salt and cerium salt where the percentage of lanthanum is greater than the percentage of cerium. The preferred ratio of the percentage of lanthanum to the percentage of cerium is at least 2.0. In other embodiments, the rare earth metal salt is a mixture of lanthanum salt and cerium salt where the percentage of cerium is greater than the percentage of lanthanum.

In some embodiments, the active salt composition comprises an alkaline metal salt or oxide. The alkaline metals in the alkaline metal salts can be magnesium, calcium, strontium, and barium. Preferably, the alkaline metals are magnesium and barium. The most preferred alkaline metal is magnesium. The preferred alkaline metal salts are alkaline metal chlorides. However, other alkaline metal salts or oxides which would convert into the chloride salts during the oxychlorination process can also be used, e.g., carbonate salts, nitrate salts and other halide salts like bromide salts. The amount of the alkaline metal in the alkaline metal salts can be in the range from about 0.05% to about 6% by weight based on the total weight of the oxychlorination catalyst. In some embodiments, the amount of the alkaline metal in the alkaline metal salt is in the range from about 0.25% to about 4% by weight based on the total weight of the oxychlorination catalyst. In some embodiments, the amount of the alkaline metal in the rare earth metal salt is in the range from about 0.25% to about 3% by weight based on the total weight of the oxychlorination catalyst.

Optionally, at least one other metal salt or oxide can be present in the active salt composition in relatively small amounts. Such other metal salts can be in the form of carbonate, nitrate or halide such as chloride and bromide. Non-limiting examples of such other metals include main group metals, such as lead, tin, bismuth, gallium and the like, and transition metals, such as iron, zinc, chromium, nickel, cobalt, scandium, vanadium, titanium, manganese, zirconium, silver, gold, ruthenium, rhodium, palladium and the like. In some embodiments, the amount of each metal in the other metal salts or oxides can be present in up to about 1 wt % based on the total weight of the oxychlorination catalyst. In other embodiments, the amount of each metal in the other metal salts or oxides can be present in up to about 0.5 wt % based on the total weight of the oxychlorination catalyst. In further embodiments, none of the other metal salts or oxides is present in the active salt composition.

Any method of preparing oxychlorination catalysts known to a person of ordinary skill in the art can be used to prepare the oxychlorination catalyst compositions disclosed herein. Non-limiting examples of such methods are described in PCT Patent Application No. WO 81/01284 and U.S. Pat. Nos. 3,488,398; 4,339,620; 4,446,249; 4,740,642; 4,849,393; 5,292,703; 5,382,726; 5,600,043; 6,872,684; 6,803,342; 6,777,373; 6,759,365; and 6,174,834, and Japanese Patent Publication No. 11-090233. The active salt composition can be added onto the support material by addition of a solution of the active salt composition in any suitable solvent such as water, alcohols, dimethyl formamide, dimethyl sulfoxide, ethers, and ketones. The preferred solvent is water. While any metal salts capable of forming a solution are suitable, the preferred metal salts are the chloride salts. One non-limiting example of preparing the oxychlorination catalyst includes the step of dissolving in water an active salt composition comprising one or more metal chlorides such as copper chloride, alkali metal chlorides, rare earth metal chlorides, alkaline metal chlorides, transition metal chlorides other than copper chloride and combinations thereof The solution can be slowly sprayed on the support material with continuous mixing (or alternatively the support material can be added to the solution with mixing) followed by drying to remove the solvent contained within the pores or on the surface of the catalyst. The drying can be performed at any suitable temperature known to a person of ordinary skill in the art. In some embodiments, the drying temperature is between about 50° C. and about 300° C., preferably between about 100° C. and about 200° C.

Alternatively, the active salt composition can be added onto the alumina support material by impregnating the support material with an aqueous solution of an active salt composition comprising one or more water soluble metal salts, and then drying the wet impregnated support material at an elevated temperature. The water soluble metal salts can be chloride, bromide, nitrate or carbonate salts of copper, alkali metals, rare earth metals, alkaline metals, transition metals other than copper and combinations thereof. In some embodiments, one or more of the metal salts are calcined on the support material to produce an oxychlorination catalyst. In other embodiments, none of the metal salts is calcined on the support material. The calcination can be performed at any suitable temperature known to a person of ordinary skill in the art. In some embodiments, the calcination temperature is between about 300° C. and about 700° C., preferably between about 350° C. and about 600° C.

When the active salt composition comprises a copper salt and at least one active metal salt such as alkali metal salts, rare earth metal salts, alkaline metal salts, transition metal salts other than a copper salt and combinations thereof, the copper salt and the active metal salt can be added, by the procedures described above or any other procedures known to a person of ordinary skill in the art, onto the support material in more than one step and in any order. In some embodiments, the active metal salt is added onto the support material prior to the addition of the copper salt. In other embodiments, the copper salt is added onto the support material prior to the addition of the active metal salt. Optionally, the active metal salt (or the copper salt) is dried or calcined before the addition of the copper salt (or the active metal salt). In other embodiments, when there are more than one active metal salt, each of the active metal salts is added onto the support material individually in a separate step. Optionally, each of the active metal salts is dried or calcined before the addition of another active metal salt. In further embodiments, each addition step may add two or more active metal salts such as copper salts, alkali metal salts, rare earth metal salts, alkaline metal salts, transition metal salts other than copper salts and combinations thereof. Based on the disclosure herein, a person of ordinary skill in the art can modify the addition steps and/or the order of the addition of the active metal salts to obtain an oxychlorination catalyst having desirable properties. Some multi-step addition or impregnation processes for the preparation of the oxychlorination catalysts are disclosed in PCT Patent Application No. WO 81/01284, U.S. Pat. Nos. 4,446,249; 6,872,684; 6,803,342; 6,777,373; 6,759,365; and 6,174,834, and Japanese Patent Publication No. 11-090233, all of which are incorporated herein by reference.

In some embodiments, the oxychlorination catalyst can be prepared by wetting the alumina support material, as above described, with an aqueous solution of an active salt composition comprising one or more metal salts such as copper salts, alkali metal salts, rare earth metal salts, alkaline metal salts, transition metal salts other than copper salts and combinations thereof. The wetted alumina support material is then dried slowly at about 80° C. to 150° C. to remove water. In particular embodiments, the metal salts and their amounts are chosen so that the final oxychlorination catalyst contains from about 2% to about 12% by weight of copper, from about 0.2% to about 3.0% by weight of the incorporated alkali metal and from about 0.1% to about 14% by weight of the rare earth metal, and from about 0.05% to about 6.0% by weight of alkaline metal, all of which are based on the total weight of the oxychlorination catalyst. In some embodiments, the total weight of metals in the oxychlorination catalysts for fixed-bed catalysis can be between about 2.5% and about 35%, between about 3% and about 30%, between about 3% and about 25%, or between about 4% and about 25%, based on the total weight of the oxychlorination catalyst.

The oxychlorination catalyst can have a surface area between about 25 $m^2/g$ and about 300 $m^2/g$, as determined by the BET method. In some embodiments, the surface area of the oxychlorination catalyst is between about 50 m²/g and about 250 m²/g. In other embodiments, the surface area of the oxychlorination catalyst is between about 70 m²/g and about 250 m²/g. In further embodiments, the surface area of the oxychlorination catalyst is between about 50 m²/g and about 200 m²/g. In certain embodiments, the surface area of the oxychlorination catalyst is between about 70 m²/g and about 150 m²/g.

The oxychlorination catalyst can have an average particle size ranging from about 5 to about 300 microns, from about 20 to about 250 microns, from about 20 to about 200 microns, from about 20 to about 150 microns, from about 20 to about 120 microns, from about 30 to about 100 microns, or from about 30 to about 90 microns. The compacted or tamped bulk density of the oxychlorination catalyst can vary between about 0.6 and about 1.6 g/cc, between about 0.7 and about 1.5 g/cc, between about 0.7 and about 1.3 g/cc, or between about 0.8 and about 1.3 g/cc.

The oxychlorination catalyst composition comprises a diluent. In general, a diluent can be used to assist in control of the heat of reaction and to reduce the levels of oxidation by-products ($CO$ and $CO_2$) and chlorinated by-product formation. Unexpectedly, as disclosed herein, some oxychlorination catalyst compositions comprising an oxychlorination catalyst and a diluent having the proper chemistry and/or characteristics can increase the optimal operating temperature of the oxychlorination process while maintaining product selectivity or purity. As disclosed herein, the optimal operating temperature for the catalyst in reactors where the majority of the vent gas is recycled back to the reactor is the point where the HCl conversion and the ethylene selectivity are optimized. For air-based, once-through reactors, the optimal operating temperature is the point where the HCl conversion and the ethylene efficiency are optimized. For any given oxychlorination reactor, catalyst charge and production rate, the optimum operating temperature, $T_{opt}$, is that specific reactor control temperature which, when used in conjunction with the optimized $HCl/C_2H_4/O_2$ reactor feed ratios, will result in the most economical balance between ethylene efficiency (or ethylene selectivity for recycle operations), HCl conversion (which may impact neutralization costs), HCl efficiency, crude EDC purity (which may impact by-product separation and disposal costs), and fuel gas value of the vented gases (when remaining ethylene is used as a fuel gas in a gas incinerator). The most economical balance is determined by minimizing the combined cost of the total losses of chlorine, ethylene, caustic, and crude EDC as liquid by-product for a particular reactor. For any oxychlorination process using a given reactor and an oxychlorination catalyst without a diluent, the optimum operating temperature of such a process is defined herein as $T_{opt(1)}$. For any oxychlorination process using a given reactor and an oxychlorination catalyst with a diluent, the optimum operating temperature of such a process is defined herein as $T_{opt(2)}$. In some embodiments, $T_{opt(2)}$ is higher than $T_{opt(1)}$ given that the reactor, quantity of the reactor charge (i.e., either the oxychlorination catalyst or the oxychlorination catalyst with diluent) and production rates (lbs/hr of pure EDC produced) are the same.

The $T_{opt(2)}$ of an oxychlorination process using the oxychlorination catalyst composition disclosed herein can be higher than the $T_{opt(1)}$ of a corresponding oxychlorination process using the same reactor, reactants, quantity of the reactor charge, production rates and oxychlorination catalyst but without the diluent (e.g., alumina silicate) disclosed herein. In some embodiments, the $T_{opt(2)}$ of the oxychlorination process using the oxychlorination catalyst composition disclosed herein is at least about 1° C., at least about 5° C., at least about 10° C., at least about 15° C., at least about 20° C., at least about 25° C., or at least about 30° C. higher than the $T_{opt(1)}$ of the corresponding oxychlorination process without the diluent (e.g., alumina silicate) disclosed herein using the same reactor, reactants, quantity of the reactor charge, production rates and oxychlorination catalyst.

In general, any catalytically and chemically inert particles that are thermally stable at the optimal operating temperature employed, can be used as a diluent in the oxychlorination catalyst composition disclosed herein. In some embodiments, the optimum operation temperature varies between about 170° C. and about 350° C., between about 180° C. and about 320° C., between about 190° C. and about 300° C., between about 190° C. and about 250° C., or between about 210° C. and about 250° C. Non-limiting examples of suitable diluents include particles of alumina silicates, glass beads, silica, ballotini, alumina, graphite, and silicon carbide. The diluent can be chemically similar to or different from the support material of the oxychlorination catalyst. In some embodiments, the diluent is chemically the same as the support material. In other embodiments, the diluent is chemically different from the support material.

In some embodiments, the diluent comprises particles of an alumina silicate (also known as aluminum silicate or aluminium silicate). Alumina silicates suitable for this invention can include, but are not limited to, hydrated alumina silicates, hydroxylated alumina silicates, dehydroxylated or anhydrous alumina silicates, and combinations thereof. Some non-limiting examples of hydrated alumina silicates include compounds having the formula $Al_2O_3.2SiO_2.2H_2O$ such as kaolin, china clay, kaolinite, dickite, nacrite, kaopectate and porcelain clay, compounds having the formula $Al_2O_3.2SiO_2.4H_2O$ such as halloysite, and combinations thereof. Some non-limiting examples of hydroxylated alumina silicates can include compounds having the formula $Al_2(Si_2O_5)_2(OH)_2$ such as pyrophyllite, compounds having the formula $Al_2(Si_4O_{10})_2(OH)_2$ such as montmorillonite, and combinations thereof. Some non-limiting examples of dehydroxylated or anhydrous alumina silicates include compounds having the formula $Al_2O_3.SiO_2$ such as kyanite, andalusite and sillimanite, compounds having the formula $Al_2O_3.2SiO_2$ such as metakaolin, compounds having the formula $3Al_2O_3.2SiO_2$ such as mullite, and combinations thereof. Each of the alumina silicates may comprise small amounts of accessory minerals or impurities. The accessory minerals are minerals that may be present in minor amounts in alumina silicates and are not considered as essential constituents of the alumina silicates. Any natural mineral that is not an alumina silicate may be present in the alumina silicates disclosed herein as an accessory mineral. Non-limiting examples of such accessory minerals include titanium oxide (e.g., anatase and rutile), feldspar, iron oxides (e.g., $Fe_2O_3$), sodium salts, potassium salts, calcium oxide, magnesium oxide, mica, montmorillonite and quartz. In some embodiments, the amount of each of the accessory minerals or impurities in the alumina silicate may be from about 0.01 wt % to about 10 wt %, from about 0.05 wt % to about 7.5 wt %, or from about 0.1 wt % to about 5 wt % of the total weight of the alumina silicate. In other embodiments, the alumina silicates disclosed herein do not contain an accessory mineral or impurity.

The alumina silicates can be metal alumina silicates which may contain other metal ions in addition to $Al^{3+}$. Some non-limiting examples of metal ions include alkali metal ions, alkaline metal ions, transition metal ions and combinations thereof. In some embodiments, the metal ions are $Li^+$, $Na^+$, $K^+$, $Rb^+$, $Cs^+$, $Be^{2+}$, $Ca^{2+}$, $Mg^{2+}$, $Sr^{2+}$, $Ba^{2+}$, $Co^{2+}$, $Ni^{2+}$, $Cu^{2+}$, $Sn^{2+}$, $Zn^{2+}$, $Mn^{2+}$, $Pb^{2+}$, $Fe^{2+}$, $Fe^{3+}$ and the like. Some non-limit examples of metal alumina silicates include magnesium alumina silicate, calcium alumina silicate, sodium alumina silicate, beryllium alumina silicate, potassium alumina silicate, and the like. In some embodiments, the alumina silicate disclosed herein comprises no metal ion other than $Al^{3+}$. In other embodiments, the alumina silicate disclosed herein is free of alkali metal ion, alkaline metal ion, transition metal ion or a combination thereof. In further embodiments, the alumina silicate disclosed herein is free of alkaline metal ion. In additional embodiments, the alumina silicate disclosed herein is free of magnesium ion.

The alumina silicates can be classified according to their layer structures. For example, alumina silicates having a two-layer (i.e., 1:1) structure may include, but are not limited to, kaolin, kyanite, andalusite and sillimanite. Alumina silicates having a three-layer (i.e., 2:1) structure may include, but are not limited to, halloysite, pyrophyllite and montmorillonite. Alumina silicates having a four-layer (i.e., 2:1:1) structure may include, but are not limited to, chlorite. The diluent suitable for this invention can also include other alumina silicate compounds which have only approximated or undetermined formulae such as allophanes and imogolite.

The alumina silicate can include dehydroxylated, dehydrated and/or calcined products such as metakaolin or mullite obtained by dehydroxylating, dehydrating and/or calcining the hydrated alumina silicates, such as kaolin, kaolinite, dickite, nacrite and halloysite, at a temperature between about 200° C. and about 1250° C. for about 5 minutes to about 7 days. Hereinafter, the terms kaolin, kaolinite, dickite, nacrite and halloysite may include the corresponsding hydrated or partially hydrated forms as well as the above-mentioned dehydroxylated, dehydrated and/or calcined products. In some embodiments, the kaolin, kaolinite, dickite, nacrite or halloysite is hydrated or partially hydrated. In further embodiments, the kaolin, kaolinite, dickite, nacrite or halloysite is totally dehydrated and thus anhydrous. In other embodiments, the alumina silicate disclosed herein is dehydroxylated, dehydrated or calcined kaolin such as metakaolin (i.e., $Al_2O_3 \cdot 2SiO_2$), $Si_3Al_4O_{12}$, mullite (i.e., $3Al_2O_3 \cdot 2SiO_2$), or a combination thereof. Furthermore, the dehydroxylated, dehydrated or calcined kaolin may comprise small amounts of accessory minerals as disclosed above.

The kaoliens disclosed herein can be prepared according to a multi-step process as outlined in Scheme A below. Each step in Scheme A is optional. For example, if spray drying is used for the drying step and spray drying can be used to control or obtain the desirable particle size, then the classification step becomes optional and can be omitted. In some embodiments, the calcining temperature in the calcination step is above about 500° C., about 600° C., about 700° C., about 800° C., about 900° C., about 1000° C., about 1100° C., about 1200° C., about 1300° C., about 1400° C., about 1500° C., about 1600° C., about 1700° C., about 1800° C., or about 1900° C. In further embodiments, the calcining temperature is below about 600° C., about 700° C., about 800° C., about 900° C., about 1000° C., about 1100° C., about 1200° C., about 1300° C., about 1400° C., about 1500° C., about 1600° C., about 1700° C., about 1800° C., about 1900° C., or about 2000° C. In other embodiments, the calcining temperature can be between about 500° C. and about 2000° C., between about 600° C. and about 1900° C., between about 700° C. and about 1800° C., between about 800° C. and about 1700° C., between about 900° C. and about 1600° C., between about 1000° C. and about 1500° C., between about 1100° C. and about 1500° C., between about 1200° C. and about 1500° C., between about 1100° C. and about 1400° C., between about 1200° C. and about 1400° C. or between about 1300° C. and about 1400° C. Further, each step can be carried out in any manner known to persons skilled in the art, such as those described in U.S. Pat. Nos. 6,943,132, 6,942,784, 6,942,783, 6,908,603, 6,787,501, 6,696,378, 6,652,642, 6,585,822, 6,379,452, 6,346,145, 6,136,086, 6,103,005, 5,997,626, 5,968,250, 5,856,397, 5,522,924, 5,395,809, 5,393,340, 5,261,956, 5,129,953, 5,112,782, 5,061,461, 5,074,475, 5,028,268, 5,023,220, 5,011,534, 5,006,574, 4,678,517, 4,578,118, 4,525,518, 4,427,450, and 4,246,039, all of which are incorporated herein by reference in their entirety. The preparation of kaolins are also described in Kogel et al., "*The Georgia Kaolins: Geology and Utilization*," the Society for Mining Metallurgy & Exploration (2002), which is incorporated herein by reference in its entirety.

Scheme A

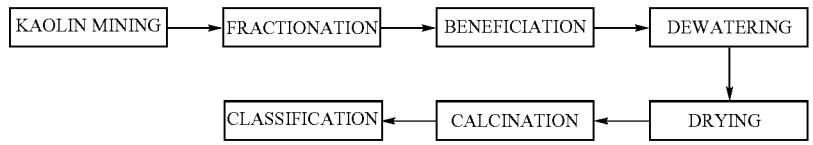

In some embodiments, the kaolin disclosed herein can be prepared according to following procedure. The kaolin is mined, mixed with water to form a slurry, and then fractionated into platelets having an average particle size from about 0.1 to about 10 microns, from about 0.25 to about 5 microns, from about 0.5 to about 3 microns, or from about 0.75 to about 2 microns. The resulting kaolin slurry then undergoes a water removal and spray drying process to form microspheres of the desired particle size that are then calcined at a temperature from about 850° C. to about 1300° C., from about 900° C. to about 1200° C. from about 950° C. to about 1100° C. to fuse the platelets having improved attrition resistance.

In other embodiments, the kaolin is in the form of microspheres which can be prepared according to the general procedures disclosed in U.S. Pat. Nos. 4,493,902, 6,942,784, 6,943,132 and 7,101,473, all of which are incorporated herein by reference. A mixture of hydrous kaolin and/or metakaolin and kaolin that that has been calcined at least substantially through its characteristic exotherm can be mixed with water to form an aqueous slurry. The characteristic exotherm of kaolin has been reported in the literature such as the article by Zheng et al., "*Effect of Properties of Calcined Microspheres of Kaolin on the Formation of NaY Zeolite,*" Bulletin of the Catalysis Society of India, 4, 12-17(2005), which is incorporated herein by reference. The aqueous slurry can be then spray dried to obtain microspheres comprising a mixture of the hydrous kaolin and/or metakaolin and calcined kaolin. optionally, a moderate amount of a metal silicate can be added to the aqueous slurry before it is spray dried. Some nonlimiting examples of suitable metal silicates include alkali silicates (e.g., sodium silicate, potassium silicate), alkaline silicates (e.g., magnesium silicate and calcium silicate), transitional metal silicates (e.g., titanium silicate and iron silicate) and combinations thereof. In some embodiments, the amount of the metal silicate added to the kaolin is from about 0 wt % to about 10 wt %, from about 0.05 wt % to about 8 wt %, or from about 0.1 wt % to about 6 wt %, based on the total weight of the kaolin. In certain embodiments, the kaolin does not contain a metal silicate.

After spray drying, the microspheres can be calcined directly, or alternatively acid-neutralized. The acid-neutralization process comprises co-feeding uncalcined, spray dried microspheres and mineral acid to a stirred slurry at controlled pH. The rates of addition of solids and acid are adjusted to maintain a pH of about 2 to about 7. In some embodiments, the pH is maintained at about 2.5 to about 4.5, with a target pH of about 3. A metal silicate such as sodium silicate can be gelled to silica and a soluble sodium salt, which is subsequently filtered and washed free from the microspheres. The silica gel-bound microspheres are then calcined.

In either the direct calcination or acid-neutralization process, the calcination can be carried at a temperature from about 500° C. to about 800° C. or about 550° C. to about 650° C. and for a time from 30 minutes to 8 hours in a muffle furnace sufficient to convert any hydrated kaolin component of the microspheres to metakaolin, leaving the previously calcined kaolin components of the microspheres essentially unchanged. The resulting calcined porous microspheres comprise a mixture of metakaolin and kaolin calcined through its characteristic exotherm in which both the metakaolin and the previously calcined kaolin are present in the same microspheres. Alternatively, the porous microspheres obtained previously can be further calcined at a temperature from about 1000° C. to about 1300° C. or from about 1000° C. to about 1200° C. and for a time from 30 minutes to 8 hours in a furnace sufficient to convert part or all of the metakaolin component of the microspheres to kaolin calcined through its characteristic exotherm to form microspheres in which only calcined kaolin are present.

Similarly, the alumina silicate for this invention can include alumina silicate compounds obtained by dehydroxylating the hydroxylated alumina silicates, such as pyrophyllite and montmorillonite, at a temperature between about 200° C. and about 1250° C. for about 5 minutes to about 7 days. Hereinafter, the terms pyrophyllite and montmorillonite mean the totally dehydroxylated, partially dehydroxylated, or hydroxylated forms. In some embodiments, the pyrophyllite or montmorillonite is hydroxylated. In other embodiments, the pyrophyllite or montmorillonite is partially dehydroxylated. In further embodiments, the pyrophyllite or montmorillonite is totally dehydroxylated.

The amount of the diluent in the oxychlorination catalyst composition may be between about 5% and about 95% by weight, based on the total weight of the oxychlorination catalyst composition. In some embodiments, the amount of the diluent is between 10% and 90% by weight. In other embodiments, the amount of the diluent is between 20% and 80% by weight. In further embodiments, the amount of the diluent is between 30% and 70% by weight. In additional embodiments, the diluent is an alumina silicate such as kaolin in an amount of between about 20% and about 80% by weight based on the total weight of the oxychlorination catalyst composition.

The diluent can be of any form or shape that is suitable for catalyst applications. In some embodiments, the diluent has an irregular form or shape. In other embodiments, the diluent comprises particles having a regular shape such as sphere, cylinder, disk, bead, drum, oval, platelet, flake, needle, and the like. In further embodiments, the diluent is in the form of microspheres.

The surface area of the diluent can vary between about 0.1 $m^2/g$ to about 300 $m^2/g$, preferably between about 0.1 to about 100 $m^2/g$, more preferably between about 0.1 $m^2/g$ to about 50 $m^2/g$, most preferably between about 0.1 $m^2/g$ to less than 25 $m^2/g$, as determined by the BET method. In general, when the surface area of the diluent is less than 25 $m^2/g$, the diluent may not act as a co-catalyst or promote undesired side reactions. Not to be bound by theory, it is believed that the diluent having a small surface area and/or weaker salt-diluent versus salt-support interaction can avoid the transfer of the active catalyst components from the oxychlorination catalyst particles. In some embodiments, the diluents have a surface area less than 25 $m^2/g$. In general, the low-surface-area diluent can reduce the transfer of the active catalyst components to the diluent. In other embodiments, the diluents have a surface area greater than 25 $m^2/g$. optionally, the high-surface-area diluent may be inactivated by impregnating with sufficient metal ions, such as alkali metal ions, to reduce to an acceptable level the formation of by-products, such as ethyl chloride, vinyl chloride, 1,1,2-trichloroethane, carbon tetrachloride and dichloroethylene. In a particular embodiment, the diluent is an alumina silicate such as kaolin having a surface area between about 0.1 $m^2/g$ and less than 25 $m^2/g$, preferably between about 1 $m^2/g$ and about 20 $m^2/g$, and more preferably between about 3 $m^2/g$ and about 16 $m^2/g$, as determined by the BET method.

It is desirable that the diluent can be intimately mixed with the oxychlorination catalyst to allow for better fluidization and mixing within the reactor. This can be achieved by matching their physical properties such as bulk density, average particle size, and particle size distribution.

The average particle size of the diluent can vary from about 5 to about 300 microns, from about 20 to about 250 microns, from about 20 to about 200 microns, from about 20 to about 150 microns, from about 20 to about 120 microns, from about 30 to about 100 microns, or from about 30 to about 90 microns. In some embodiments, the average particle size of the diluent is from about 25% to about 200%, from about 50% to about 150%, or from about 75% to about 125% of the average particle size of the oxychlorination catalyst.

The compacted or tamped bulk density of the diluent can vary between about 0.6 and about 1.5 g/cc, between about 0.7 and about 1.4 g/cc, between about 0.7 and about 1.3 g/cc, or between about 0.8 and about 1.2 g/cc. In some embodiments, the tamped bulk density of the diluent is about 25% to about 200% of the tamped bulk density of the oxychlorination catalyst. In other embodiments, the tamped bulk density of the diluent is about 50% to about 150% of the tamped bulk density of the oxychlorination catalyst. In further embodiments, the tamped bulk density of the diluent is about 75% to about 125% of the tamped bulk density of the oxychlorination catalyst.

In some embodiments, the diluents are particles of alumina silicates. In further embodiments, the diluents are calcined kaolin microspheres having a surface area between 3 and 16 $m^2/g$ and a tamped bulk density between 0.8 and 1.4 g/cc. The physical properties of some suitable calcined kaolin microspheres are listed in Table 1 below.

TABLE 1

| Particle Size Distribution Data | Diluent 1 | Diluent 2 | Diluent 3 |
|---|---|---|---|
| % <16 microns | 0.79 | 0.77 | 0.00 |
| % <22 microns | 2.9 | 2.4 | 0.85 |
| % <31 microns | 8.1 | 6.1 | 3.2 |
| % <44 microns | 20 | 19 | 9.4 |
| % <88 microns | 73 | 76 | 49 |
| Attrition (wt %) | 65.8 | 4.5 | 3.5 |
| Initial Fines (wt %) | 16.7 | 3.4 | 5.7 |
| Compacted Bulk Density (g/cc) | 1.04 | 1.17 | 1.22 |
| Surface Area ($m^2/g$) | 5.7 | 6.8 | 3.2 |

Note:
Diluents 1-3 are calcined kaolin microspheres that can be prepared according to general preparation procedures as disclosed in Scheme A and paragraphs [56] to [60]; or obtained from Engelhard Corporation, Iselin, NJ.

The average particle size and the particle size distribution data were measured with a Honeywell Microtrac X-100 laser particle analyzer by the method described earlier in this specification. The bulk density can be expressed in term of compacted bulk density (CBD), sometimes referred to as tamped, tapped, or total bulk density (TBD). The bulk density of the diluent, oxychlorination catalyst or support material can be measured by the following method. A quantity of approximately 26 g of powder from each sample, dried for at least 4 hours at 110° C. and free of any agglomerates, was introduced into a 50-mL graduated cylinder. The initial volume of the packing was observed. Next, the cylinder was placed on a Tap-pak Volumeter for a 30 minute run time (about 8770 taps). The final or tapped volume of the packing was observed. The CBD or TBD of the sample was calculated by dividing the weight of the powder by the tapped volume of the packing. The attrition properties of the diluents in Table 1 above were measured by the attrition method described in the Example section below.

The attrition properties of the diluents and catalysts can be measured by ASTM D5757-00, which is incorporated herein by reference. The attrition properties of the diluents and catalysts can also be measured by a similar air-jet method that yields relative results similar to those produced by the ASTM D5757-00 method. In the air-jet method, an Air-Jet Attrition Instrument can be used. The instrument consists of a vertical tubular assembly where a calibrated volume of air (8.8 L/min) can pass through an air cup at the bottom of the assembly. Above the air cup, there is an orifice plate containing three 0.015-inch diameter holes spaced equidistant from the center at 120-degree angles. There is a sample chamber above the orifice plate having a coned interior. The cone opens upward into a 30-inch long by 1-inch inside diameter section of glass pipe. Located at the top of the glass pipe is a separation chamber having an inside diameter significantly larger than the glass pipe. An assembly holding a cellulose extraction thimble resides at the top of the separation chamber. A weighed volume of catalyst goes into the sample chamber above the orifice plate. A calibrated volume of air passes through the orifice openings at sonic speed causing the catalyst particles to collide with one another. The force of the air and the impacting action of the particles results in an initial deagglomeration/fines removal and an eventual attrition of the particles. The airflow transports particles up the glass pipe and into the separation chamber. Depending on the airflow rate and the general principles as defined by Stokes Law, particles less than the equivalent Stokes diameter pass through the chamber and are collected in the thimble. The larger particles fall back into the glass pipe. The percentage of material collected in the thimble over time determines the amount of initial fines loss in the sample and the attrition loss. The % of initial fines can be determined by collecting initial fines after 1 hour of operation and the % of attrition can be determined by collecting attrition after 5 hours of operation. It is desirable that the % of initial fines and the % of attrition of the diluent are respectively in the same order of magnitude as those of the catalyst. In some embodiments, the % attrition (or the % of initial fines) of the diluent is less than about 10 times the % attrition (or the % of initial fines) of the catalyst. In other embodiments, the % attrition (or the % of initial fines) of the diluent is less than about 5 times the % attrition (or the % of initial fines) of the catalyst. In further embodiments, the % attrition (or the % of initial fines) of the diluent is less than about 2 times the % attrition (or the % of initial fines) of the catalyst. In other embodiments, the % attrition (or the % of initial fines) of the diluent is between about 400% and about 10%, between about 200% and 25%, or between about 150% and 50% of the % attrition (or the % of initial fines) of the oxychlorination catalyst.

Oxychlorination processes are described in PCT Patent Application No. WO 81/01284, U.S. Pat. Nos. 3,488,398; 4,339,620; 4,446,249; 4,740,642; 4,849,393; 5,292,703; 5,382,726; 5,600,043; 6,872,684; 6,803,342; 6,777,373; 6,759,365; and 6,174,834, and Japanese Patent Publication No. 11-090233, all of which are incorporated herein by reference. In some embodiments, the process comprises the step of contacting a hydrocarbon such as an unsaturated hydrocarbon (e.g., ethylene), an oxygen source such as oxygen or oxygen containing gas (e.g., air), and a source of chlorine such as hydrogen chloride (HCl) with an oxychlorination catalyst composition in a reaction zone; and the step of recovering the effluent from the reaction zone. Some oxychlorination processes include once through operations where the unreacted hydrocarbon is vented or removed, and other oxychlorination processes include recycle operations wherein the unreacted hydrocarbon is recycled back to the reactor or another unit operation.

In some embodiments, the hydrocarbon is an unsaturated hydrocarbon. In other embodiments, the hydrocarbon is an olefin having 1-20 carbon atoms. In further embodiments, the olefin includes ethylene and/or propylene. In a particular embodiment, the hydrocarbon is ethylene and the oxychlorination product is 1,2 dichloroethane (ethylenedichloride or EDC).

The source of chlorine suitable for the oxychlorination process can be any compound containing chlorine which is capable of transferring its chlorine to the hydrocarbon feed. Non-limiting examples of the source of chlorine include chlorine gas, hydrogen chloride and any chlorinated hydrocarbon having one or more reactive chlorine substituents. Non-limiting examples of suitable chlorinated hydrocarbons include carbon tetrachloride, methylene dichloride and chloroform. Preferably, the source of chlorine is hydrogen chloride.

The source of chlorine may be provided to the oxychlorination process in any amount which is effective in producing the desired oxychlorination product. Typically, the source of chlorine is used in an amount equal to the stoichiometric amount required by the oxidative chlorination reaction of interest. For example, in ethylene oxychlorination, four moles of hydrogen chloride are employed per mole of oxygen. The hydrogen chloride and oxygen can be employed in amounts which are ideally selected to facilitate the near complete reaction of both reagents; but greater and lesser amounts of hydrogen chloride may also be used.

The oxygen source can be any oxygen-containing gas, such as, oxygen gas, air, oxygen enriched air, or a mixture of oxygen gas with an inert carrier gas. Generally, the feed of reactants to the oxychlorination reactor is rich in hydrocarbon relative to oxygen (i.e., hydrocarbon is in stochiometric excess).

In some embodiments, the feed comprising the hydrocarbon, source of chlorine, and source of oxygen can be diluted with an inert carrier gas, which may be any gas that does not substantially interfere with the oxychlorination process. The carrier gas may assist in removing products and heat from the reactor and in reducing the number of undesirable side-reactions. Non-limiting examples of suitable carrier gas include nitrogen, argon, helium, carbon dioxide, and mixtures thereof Generally, the amount of carrier gas used can range from about 10 to 90 mole %, and preferably from about 20 to 80 mole %, based on the total moles of the hydrocarbon, source of chlorine, source of oxygen, and inert gas diluent.

In some embodiments, the feed stream to the oxychlorination process comprises a mixture of a hydrocarbon such as ethylene, a source of chlorine such as HCl, an oxygen source, and optionally, a carrier gas. The mixture can be caused to react to form a chlorinated hydrocarbon such as EDC under process conditions sufficient to prepare the chlorinated hydrocarbon.

The oxychlorination catalyst compositions are highly efficient catalysts for the oxychlorination of an unsaturated hydrocarbon such as ethylene to a chlorinated hydrocarbon such as EDC. The temperature of the oxychlorination process can vary from about 190° C. to about 270° C., and more preferably from about 210° C. to about 260° C. The reaction pressure can vary from one atmosphere (i.e., 101 kPa) to as high as about 200 psig (i.e., 1379 kPa). The contact time in the fluid-bed and fixed-bed catalyst systems can vary from about 10 seconds to about 50 seconds, and more preferably are from about 15 to 40 seconds. As disclosed herein, the contact time is defined as the ratio of reactor volume taken up by the oxychlorination catalyst composition to the volumetric flow rate of the feed gases at the reactor control temperature and reactor top pressure.

In general, the oxychlorination reaction can be run with a mixture of a hydrocarbon, a source of chlorine and an oxygen source in any ratio and/or in any way known to a person of ordinary skill in the art. A skilled artisan can recognize that the optimum feed ratios depend on many factors such as the design of the reactors, the nature of the hydrocarbon, the nature of the source of chlorine, the nature of the oxygen source, and the like. In some embodiments, the hydrocarbon is ethylene, the source of chlorine is HCl and the oxygen source is oxygen gas. Some non-limiting examples of feed ratios of ethylene to HCl or oxygen are disclosed in U.S. Pat. Nos. 5,382,726, 6,872,684; 6,803,342; 6,777,373; 6,759,365; and 6,174,834, and Japanese Patent Publication No. 11-090233, all of which are incorporated herein by reference.

When oxychlorination catalyst compositions disclosed herein are used under commercial production conditions in the oxychlorination of ethylene to EDC, the optimum operating temperature can be increased. Higher operating temperature increases the driving force for heat removal and, therefore, allows for greater reactor productivity. In some embodiments, the optimum operating temperature can be increased by about 1 to about 30° C. without sacrificing EDC selectivity, product purity, HCl conversion and catalyst fluidity. Furthermore, all of these catalyst performance benefits are obtained simultaneously without any need to sacrifice one benefit for another.

EXAMPLES

The following examples are presented to exemplify embodiments of the invention. All numerical values are approximate. When numerical ranges are given, it should be understood that embodiments outside the stated ranges may still fall within the scope of the invention. Specific details described in each example should not be construed as necessary features of the invention.

The examples below were developed using a laboratory fluid-bed reactor operated at atmospheric pressure. However, a person of ordinary skill in the art can recognize that the oxychlorination catalyst compositions disclosed herein and their improved performances can be directly applicable to commercial plant reactor operations, on a relative basis, even though the commercial plant reactors typically are operated at elevated temperatures and pressures.

The oxychlorination catalyst compositions are evaluated based upon a number of criteria including optimal operating temperature, ethylene conversion, HCl conversion, EDC selectivity, carbon dioxide and carbon monoxide formation, and triane (1,1,2-trichloroethane) formation. The ethylene conversion or HCl conversion are the amount in mole % of ethylene or HCl consumed respectively in the oxychlorination reactor. The selectivity of a compound, on a C2 (i.e., ethylene) basis, is the yield in mole % of the compound formed in the oxychlorination reaction relative to the moles of ethylene consumed. The ethylene efficiency is the product of the ethylene conversion and the EDC selectivity. For example, a 99% ethylene conversion and a 95% EDC selectivity would result in a 94% ethylene efficiency.

In the experiments, gaseous reactants, i.e, ethylene, oxygen, and hydrogen chloride were fed to the oxychlorination reactor in molar ratios of about 1.0 mole ethylene, about 0.7 mole oxygen, and about 1.9 moles hydrogen chloride. In addition to the reactant gases, about 3.0 moles of nitrogen was added as an inert carrier gas. For all examples below, the total feed rate of the reactants and nitrogen remained constant, and the same oxychlorination reactors and sampling systems were used during data collection. This allows the comparison of the oxychorination catalyst compositions under identical conditions. As a result the differences in performance are not due to experimental design but actual differences in the performance of various oxychlorination catalyst compositions. The oxychlorination reactions were conducted at temperatures in the range of about 200° C. to about 260° C. by passing the reactants through the oxychlorination catalyst bed to produce EDC. The contact times ranged from about 13 to about 17 seconds over the temperatures tested. The contact time is defined as the ratio of reactor volume taken up by the oxychlorination catalyst composition to the volumetric flow rate of the feed gases at the reactor control temperature and reactor top pressure. The temperatures employed for each oxychlorination catalyst composition were chosen to include the point of desired performance for each oxychlorination catalyst composition tested. Because different oxychlorination catalyst compositions operate differently under different reaction conditions, performance results should be compared under the same conditions. Alternately, a desired performance level can be determined, and the conditions necessary to achieve the desired performance level can be compared. For a recycle operation, the optimal operating temperature corresponds to a range where HCl conversion and ethylene selectivity to EDC are both maximized. Ethylene conversion only becomes important for a once-through process where the unreacted feed gases are not recovered. Based on the disclosure described herein, a person of ordinary skill in the art should be able to find or modify the process conditions sufficiently to prepare a chlorinated hydrocarbon such as EDC from a hydrocarbon such as ethylene.

Diluent 3 was used in Examples 2-4 whereas Diluent 2 was used in Examples 5 and 7-9. The oxychlorination catalyst employed in Examples 1 to 5 was a 4-component oxychlorination catalyst according to the invention claimed in U.S. Pat. No. 5,292,703. The oxychlorination catalyst employed in Examples 6 to 9 was a 2-component oxychlorination catalyst comprising 3.8 wt % copper and 1.5 wt % magnesium on an alumina support. The physical properties of the 4-component and 2-component oxychlorination catalysts are listed in Table 2 below. The physical properties of the oxychlorination catalysts were measured by the same methods described above for the diluents.

TABLE 2

| PSD | 4-Component Catalyst | 2-Component Catalyst |
|---|---|---|
| % <88 micron | 85 | 86 |
| % <44 micron | 40 | 30 |
| % <31 micron | 23 | 10 |
| % <22 micron | 12 | 3 |
| % <16 micron | 6 | 1 |
| Initial Fines (%) | 6 | 2 |
| Attrition (%) | 4 | 4 |
| CBD (g/cc) | 1.02 | 1.02 |
| Surface Area ($m^2$/g) | 119 | 123 |

Example 1 (Comparative)

In this example the oxychlorination catalyst contained 4.3 wt % copper, 1.4 wt % magnesium, 1.2 wt % potassium and 2.3 wt % of a rare earth mixture with a La to Ce ratio of 2.9 to 1 on a high-surface-area alumina support material. The performance test results, at the reaction temperatures indicated, are shown in Table 3.

TABLE 3

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 210 | 93.31 | 97.32 | 98.82 | 0.943 | 0.199 |
| 215 | 94.86 | 98.77 | 98.43 | 1.297 | 0.211 |
| 225 | 96.46 | 99.28 | 96.83 | 2.748 | 0.332 |
| 230 | 97.32 | 99.14 | 95.68 | 3.785 | 0.401 |

Example 2

In this example, an oxychlorination catalyst composition comprising 80 wt % of substantially the same oxychlorination catalyst as described in Example 1 and 20 wt % of Diluent 3. The oxychlorination catalyst composition of Example 2 was tested for its catalytic properties and the results are reported in Table 4.

TABLE 4

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 215 | 93.53 | 98.38 | 99.03 | 0.757 | 0.189 |
| 220 | 95.12 | 99.24 | 98.46 | 1.261 | 0.235 |
| 230 | 97.00 | 99.32 | 96.76 | 2.758 | 0.380 |
| 235 | 97.14 | 99.40 | 95.43 | 3.951 | 0.433 |

Example 3

In this example an oxychlorination catalyst composition comprising 40 wt % of substantially the same oxychlorination catalyst as described in Example 1 was mixed with 60 wt % of Diluent 3. The oxychlorination catalyst composition of Example 3 was tested for its catalytic properties and the results are reported in Table 5.

TABLE 5

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 225 | 92.61 | 97.13 | 99.45 | 0.393 | 0.156 |
| 230 | 94.32 | 98.75 | 98.89 | 0.785 | 0.212 |
| 235 | 95.08 | 99.44 | 98.35 | 1.345 | 0.264 |
| 240 | 95.56 | 99.27 | 97.38 | 2.170 | 0.352 |
| 245 | 96.01 | 98.95 | 96.34 | 3.075 | 0.448 |

Example 4

In this example an oxychlorination catalyst composition comprising 20 wt % of substantially the same oxychlorination catalyst as described in Example 1 and 80 wt % of Diluent 3 was prepared. The oxychlorination catalyst composition of Example 4 was tested for its catalytic properties and the results are reported in Table 6.

TABLE 6

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 240 | 94.00 | 98.44 | 99.01 | 0.738 | 0.233 |
| 245 | 94.71 | 99.26 | 98.52 | 1.118 | 0.325 |
| 250 | 95.45 | 99.12 | 97.71 | 1.828 | 0.379 |
| 255 | 95.75 | 99.44 | 97.15 | 2.300 | 0.432 |

Example 5

In this example an oxychlorination catalyst composition comprising 10 wt % of substantially the same oxychlorination catalyst as described in Example 1 and 90 wt % of Diluent 2 was prepared. The oxychlorination catalyst composition of Example 5 was tested for its catalytic properties and the results are reported in Table 7.

TABLE 7

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 265 | 94.82 | 97.92 | 96.72 | 2.563 | 0.539 |
| 260 | 94.99 | 98.23 | 97.80 | 1.685 | 0.387 |
| 255 | 94.13 | 97.79 | 98.59 | 1.046 | 0.307 |
| 250 | 92.97 | 97.17 | 99.14 | 0.600 | 0.216 |

Example 6 (Comparative)

In this example the catalyst was an oxychlorination catalyst containing 3.8 wt % copper and 1.5 wt % magnesium on an alumina support. There was no diluent. The performance test results, at the reaction temperatures indicated, are shown in Table 8.

TABLE 8

| Temperature ° C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 210 | 93.20 | 97.84 | 99.09 | 0.808 | 0.093 |
| 215 | 95.06 | 98.38 | 98.22 | 1.640 | 0.129 |
| 220 | 96.18 | 98.90 | 97.31 | 2.482 | 0.176 |

TABLE 8-continued

| Temperature °C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 225 | 97.35 | 98.80 | 95.65 | 4.034 | 0.271 |
| 230 | 98.08 | 98.51 | 94.15 | 5.425 | 0.348 |

Example 7

In this example an oxychlorination catalyst composition comprising 90 wt % of substantially the same oxychlorination catalyst as described in Example 6 and 10 wt % of Diluent 2 was prepared. The oxychlorination catalyst composition of Example 7 was tested for its catalytic properties and the results are reported in Table 9.

TABLE 9

| Temperature °C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 215 | 94.22 | 97.93 | 98.70 | 1.213 | 0.075 |
| 220 | 95.72 | 98.67 | 97.67 | 2.166 | 0.148 |
| 225 | 97.18 | 98.62 | 96.51 | 3.200 | 0.250 |
| 230 | 98.14 | 98.64 | 95.21 | 4.390 | 0.342 |

Example 8

In this example an oxychlorination catalyst composition comprising 50 wt % of substantially the same oxychlorination catalyst as described in Example 6 and 50 wt % of Diluent 2 was prepared. The oxychlorination catalyst composition of Example 8 was tested for its catalytic properties and the results are reported in Table 10.

TABLE 10

| Temperature °C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 220 | 92.78 | 96.68 | 99.24 | 0.646 | 0.108 |
| 225 | 94.87 | 98.35 | 98.69 | 1.149 | 0.155 |
| 230 | 95.81 | 98.71 | 97.87 | 1.883 | 0.234 |
| 235 | 96.89 | 98.64 | 96.54 | 3.141 | 0.293 |
| 240 | 97.82 | 98.19 | 95.18 | 4.397 | 0.391 |

Example 9

In this example an oxychlorination catalyst composition comprising 20 wt % of substantially the same oxychlorination catalyst as described in Example 6 and 80 wt % of Diluent 2 was prepared. The oxychlorination catalyst composition of Example 9 was tested for its catalytic properties and the results are reported in Table 11.

TABLE 11

| Temperature °C. | Ethylene Conversion (%) | HCl Conversion (%) | EDC Selectivity (%) | CO + CO2 Selectivity (%) | 1,1,2-Triane Selectivity (%) |
|---|---|---|---|---|---|
| 240 | 92.48 | 96.30 | 98.64 | 1.123 | 0.236 |
| 245 | 94.26 | 97.04 | 97.87 | 1.819 | 0.303 |
| 250 | 95.55 | 97.42 | 96.45 | 3.124 | 0.402 |
| 255 | 96.57 | 97.70 | 95.39 | 3.956 | 0.523 |

The results of Examples 1 through 4 are graphically represented in FIGS. 1-4 which show that the oxychlorination catalyst compositions of Examples 2-4 allow higher reaction temperatures without sacrificing other important parameters of the oxychlorination process such as EDC selectivity.

FIG. 1 shows that EDC selectivity is not sacrificed when the oxychlorination catalyst of Comparative Example 1 is combined with Diluent 3 (i.e., a kaolin from Engelhard). Comparative Example 1 having no diluent has a lower selectivity for the production of EDC from ethylene. Each of Examples 2-4 which have respectively 20 wt %, 60 wt %, and 80 wt % of Diluent 3 displays a higher EDC selectivity than Comparative Example 1. Not only is the selectivity higher, but the selectivity remains high at reaction temperatures that are substantially higher.

Figure 2:
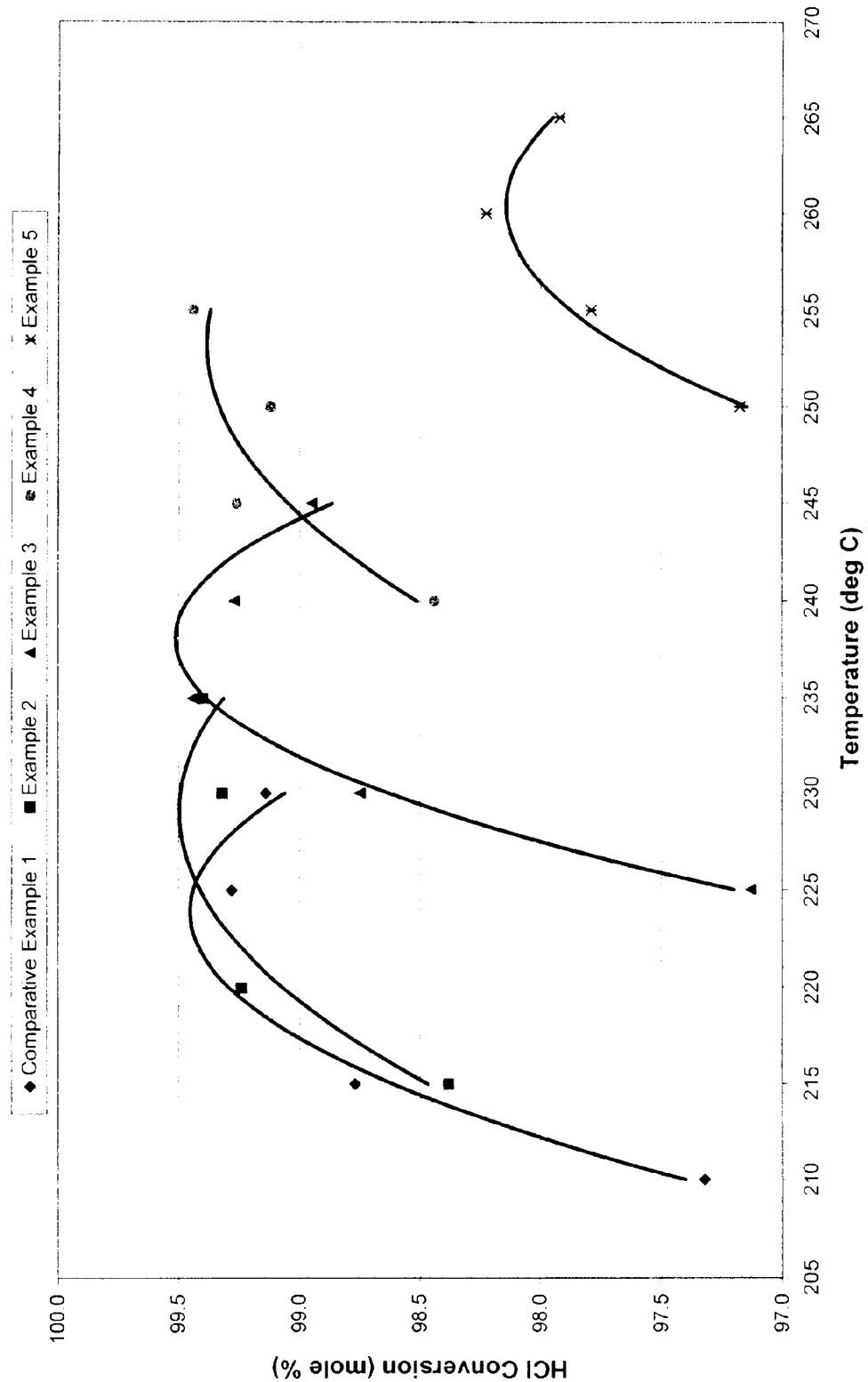
FIG. 2 depicts the HCl conversion as a function of temperature and catalyst composition of Examples 1-5 disclosed herein.

FIG. 2 compares the HCl conversion as a function of temperature. As mentioned above, high HCl conversion is desirable for a variety of reasons. FIG. 2 shows that diluted catalysts of Examples 2-4 have a maximum HCl conversion of about 99.3-99.5 percent. Yet, these maximum values are achieved at higher temperatures than that of Comparative Example 1. Consequently, Examples 2-4 can be run at higher operating temperatures without sacrificing HCl conversion.

Figure 3:
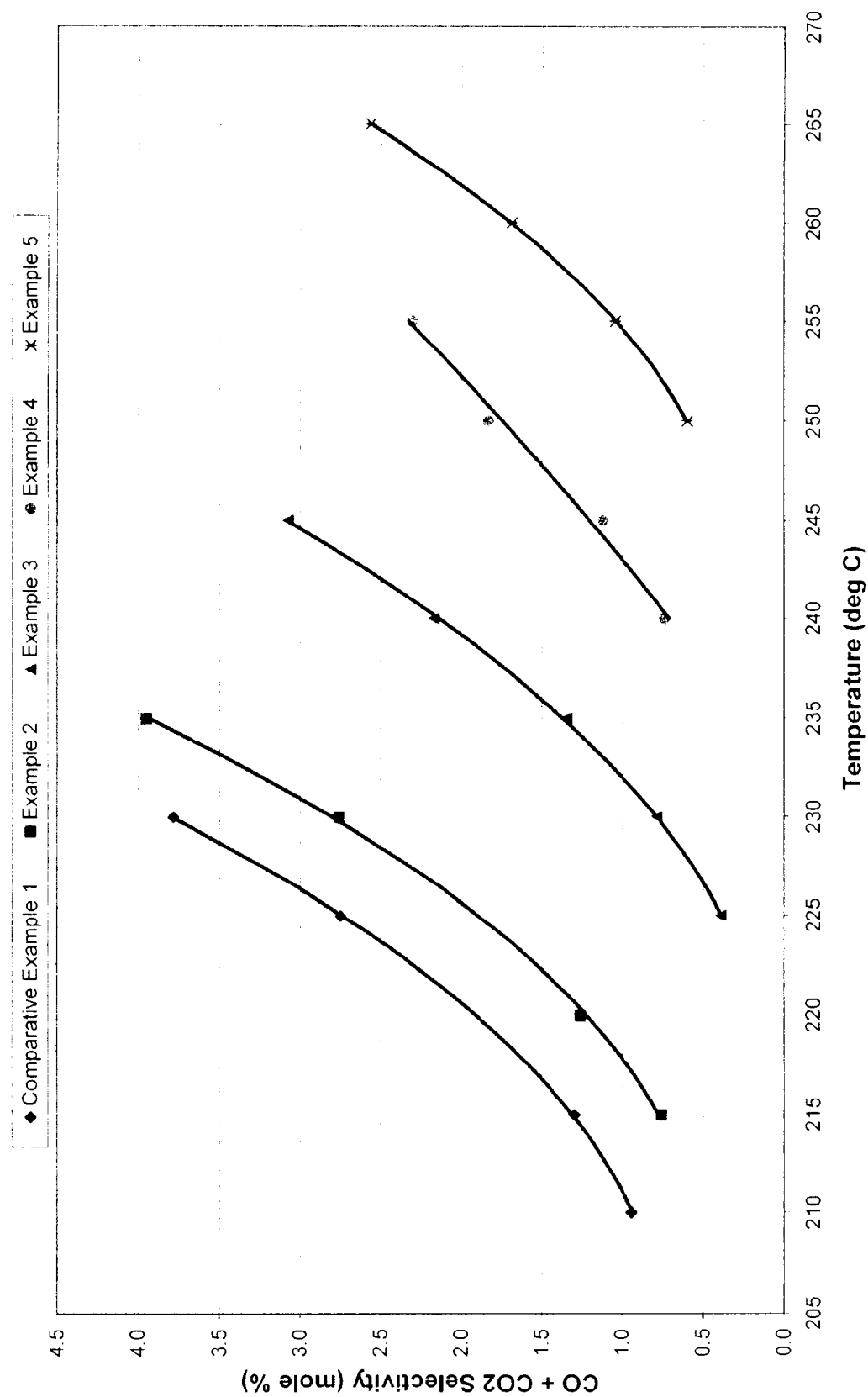
FIG. 3 depicts the carbon oxide selectivity as a function of reaction temperature and catalyst composition of Examples 1-5 disclosed herein.

As depicted in FIG. 3, the oxychlorination catalyst compositions of Examples 2-4 show acceptable carbon oxide (i.e., CO and $CO_2$) selectivity, especially at high reaction temperatures. It is shown here again that the oxychlorination catalyst compositions can be used in processes running at higher operating temperatures without increasing carbon oxide selectivity.

Figure 4:
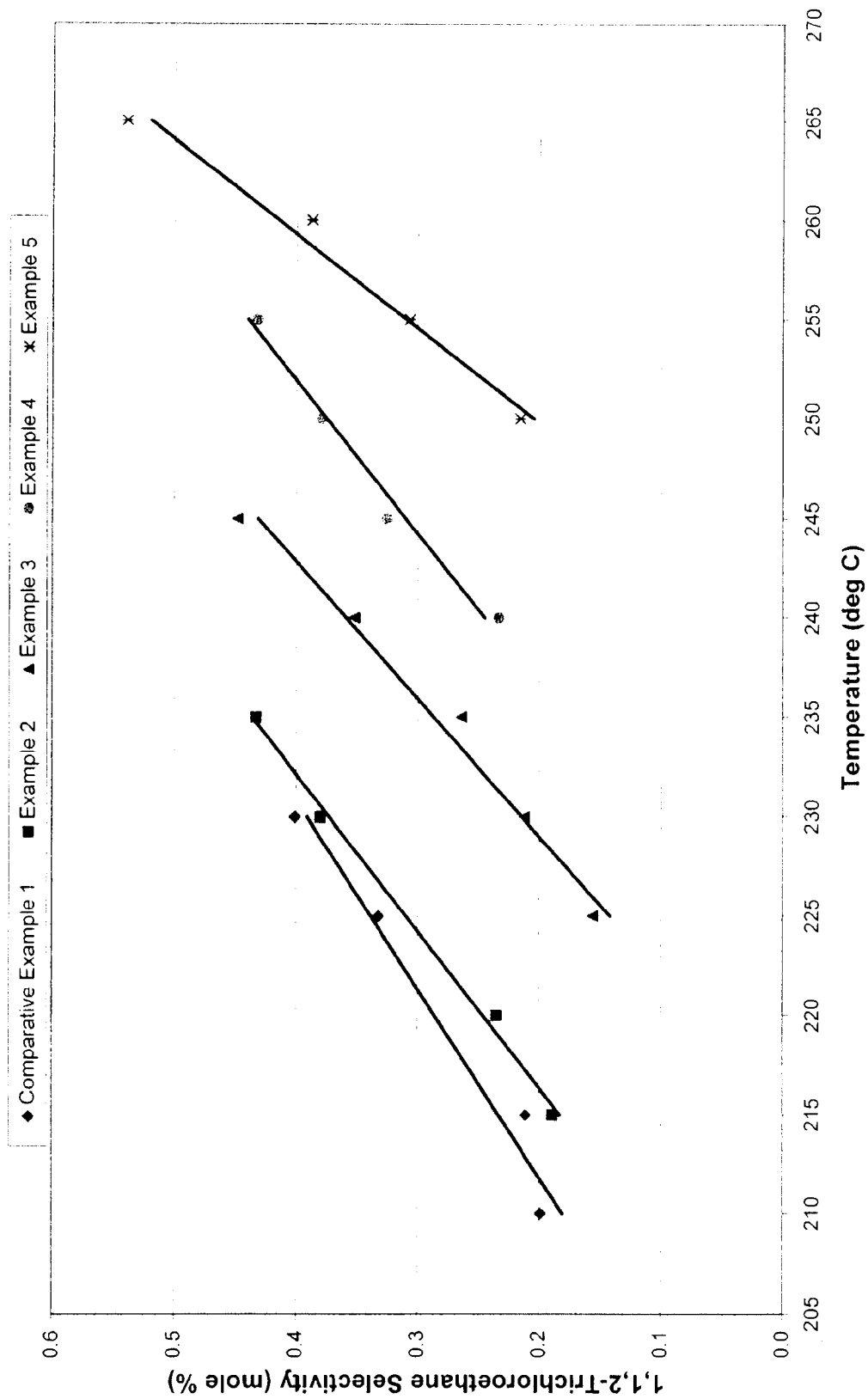
FIG. 4 depicts the 1,1,2-trichlororethane selectivity as a function of reaction temperature and catalyst composition of Examples 1-5 disclosed herein.
Figure 5:
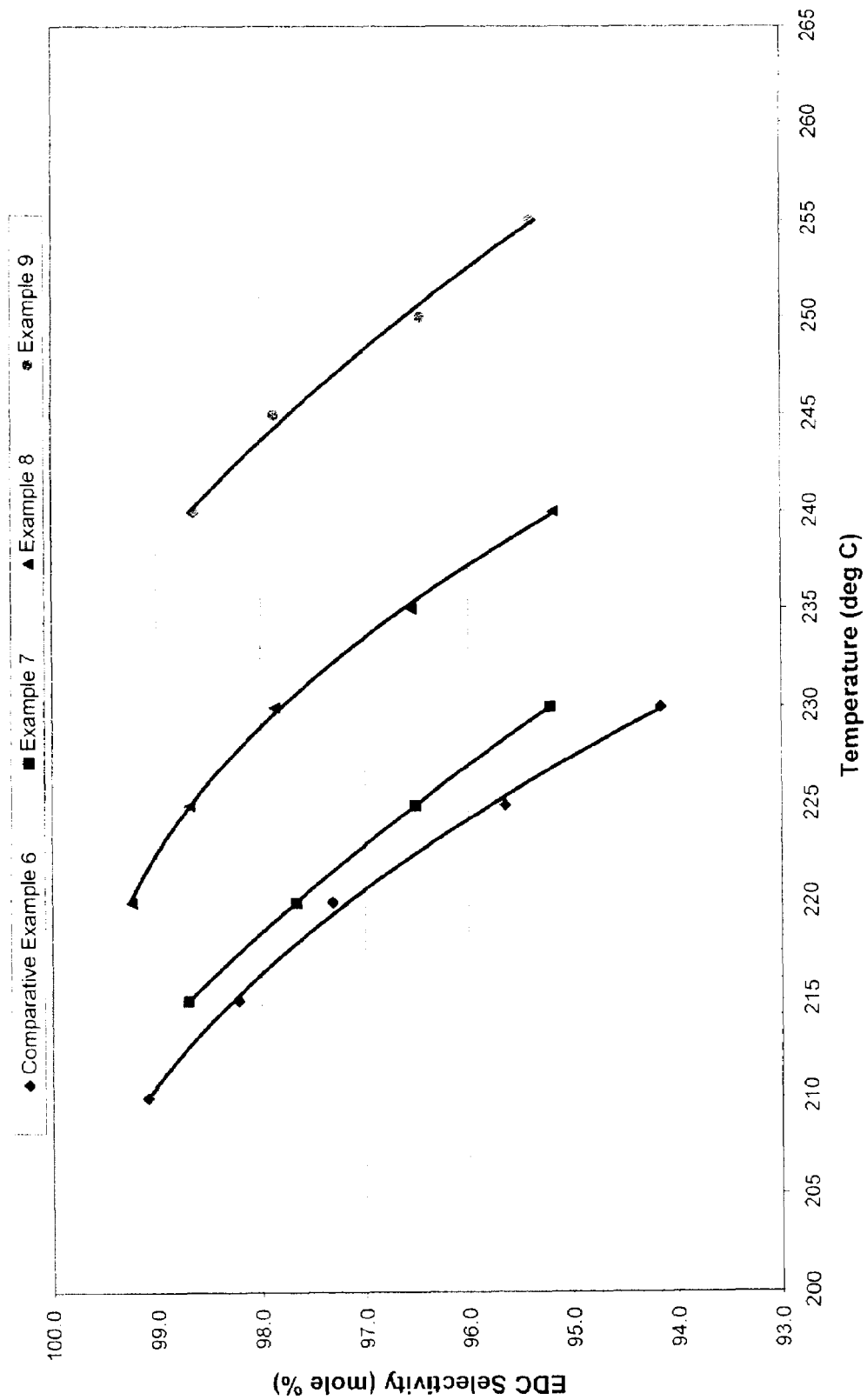
FIG. 5 depicts the EDC selectivity as function of temperature and catalyst composition of Examples 6-9 disclosed herein.
Figure 6:
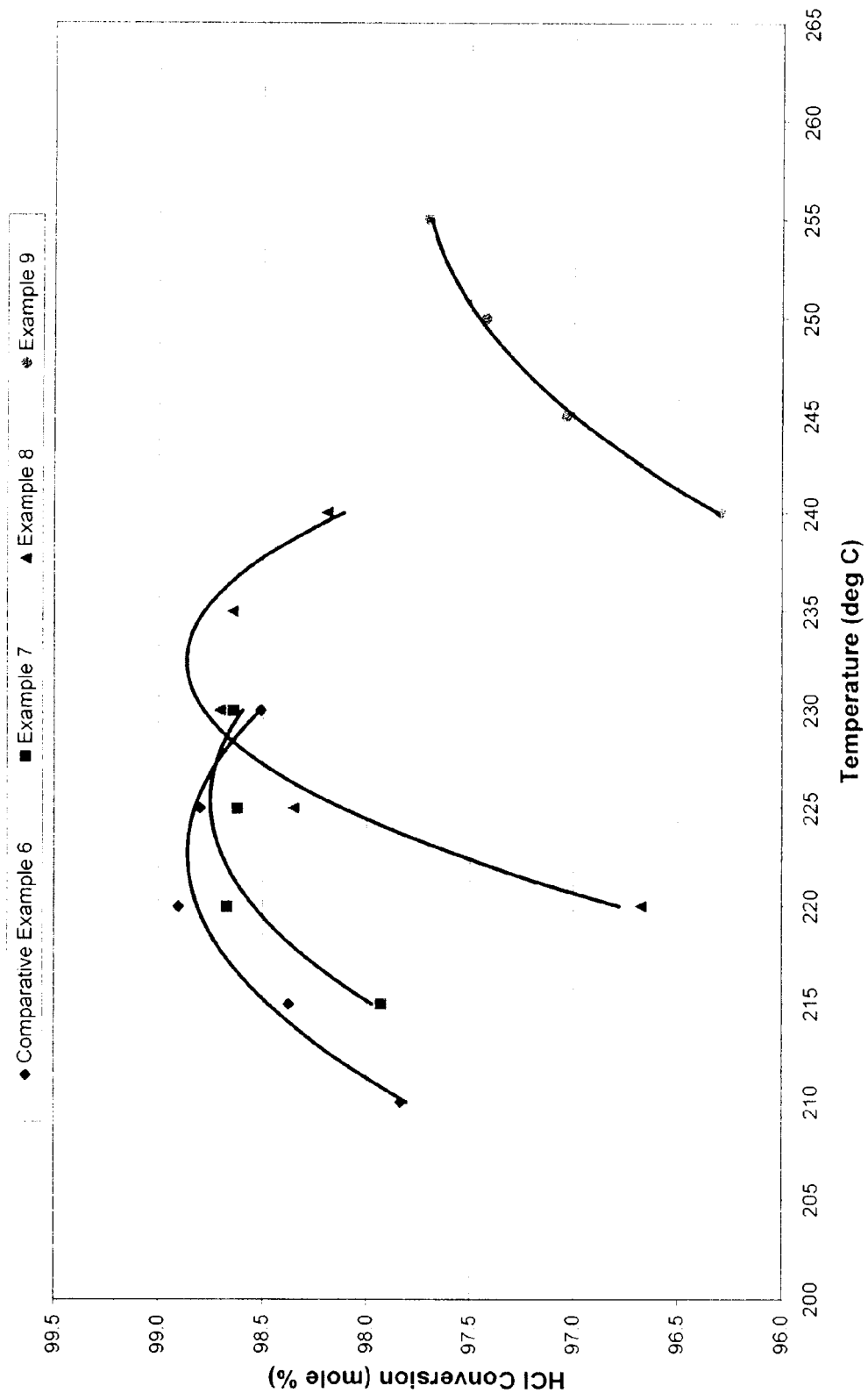
FIG. 6 depicts the HCl conversion as a function of temperature and catalyst composition of Examples 6-9 disclosed herein.
Figure 7:
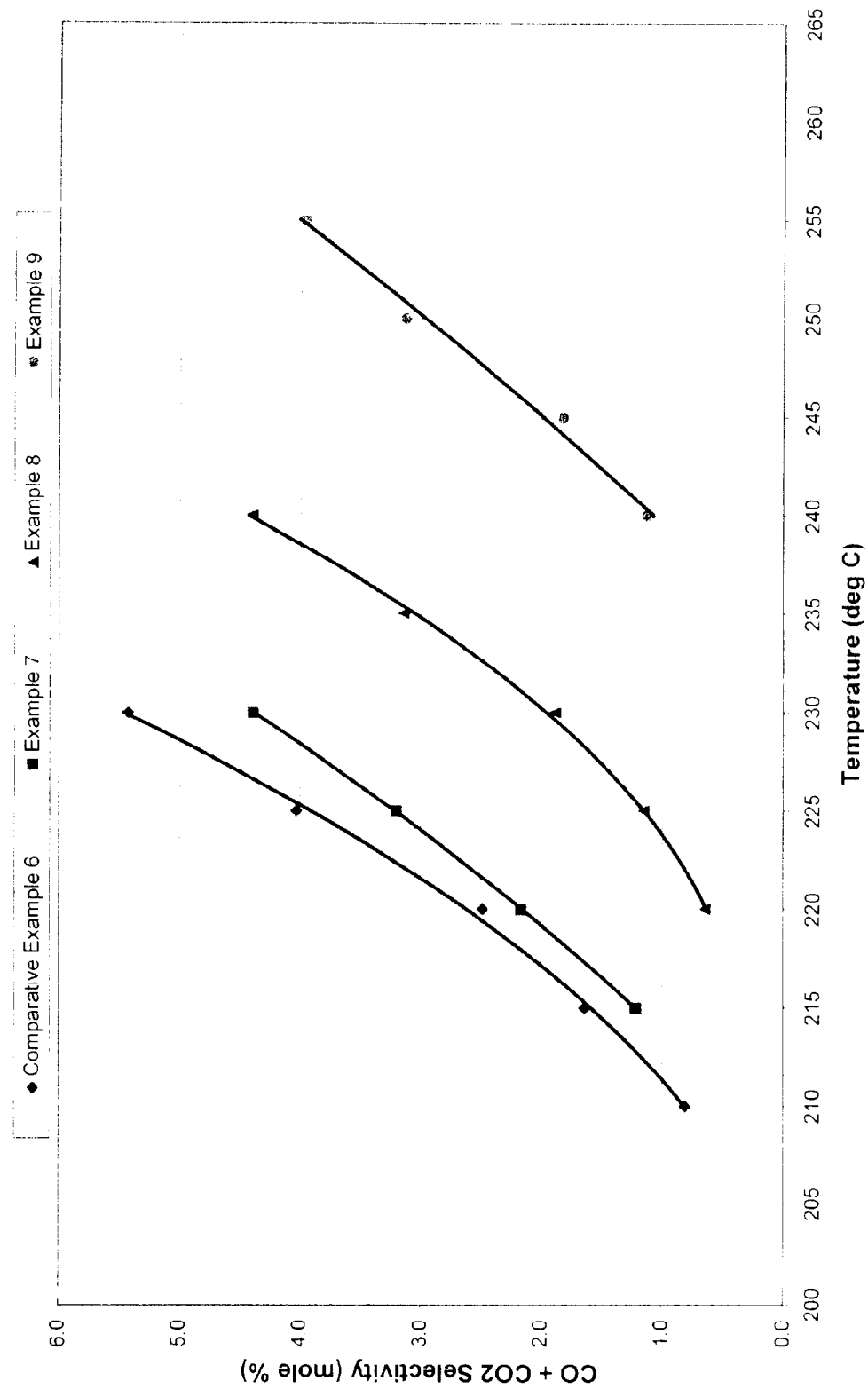
FIG. 7 depicts the carbon oxide selectivity as a function of reaction temperature and catalyst composition of Examples 6-9 disclosed herein.
Figure 8:
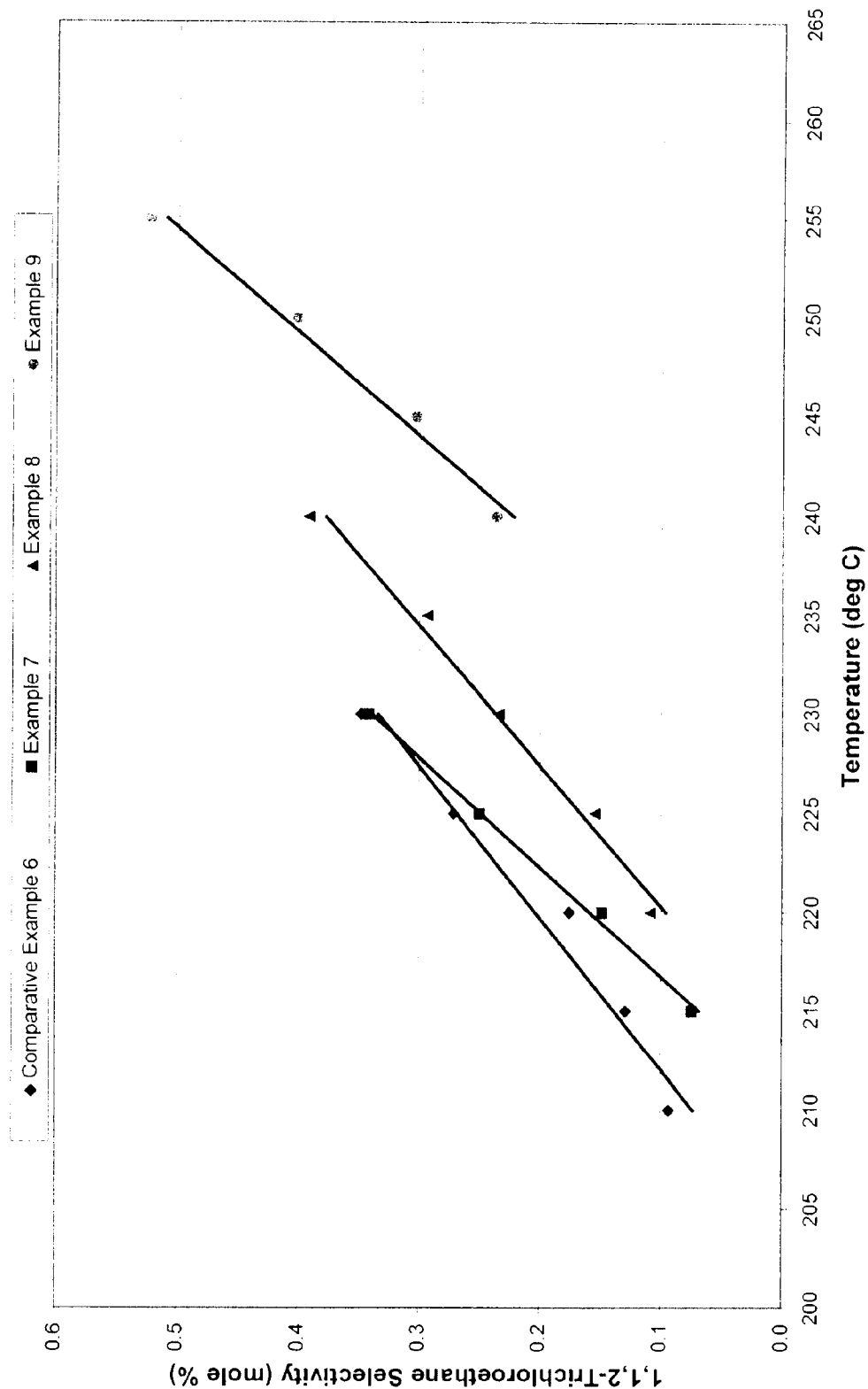
FIG. 8 depicts the 1,1,2-trichloroethane selectivity as a function of reaction temperature and catalyst composition of Examples 6-9 disclosed herein.

FIG. 4 shows that some catalysts described herein can be used in processes at increased temperatures without increasing the amount of by-products such as 1,1,2 trichloroethane (triane). Like the carbon oxide selectivity data, the triane selectivity data indicates that the oxychlorination catalyst compositions can be used at higher operating temperatures without increasing the formation of undesirable side-products.

While the invention has been described with respect to a limited number of embodiments, the specific features of one embodiment should not be attributed to other embodiments of the invention. No single embodiment is representative of all aspects of the invention. In some embodiments, the catalyst compositions may include numerous compounds not mentioned herein. In other embodiments, the compositions do not include, or are substantially free of, any compounds not enumerated herein. Some embodiments of the catalyst compositions described herein consist oft or consist essentially of, the components recited herein. Variations and modifications from the described embodiments exist. The processes described herein comprise a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling within the scope of the invention.

What is claimed is:

1. An oxychlorination catalyst composition comprising:
   (i) catalytically effective amount of an oxychlorination catalyst comprising an active salt composition distributed on a support material; and
   (ii) a diluent comprising particles of a dehydroxylated, dehydrated or calcined alumina silicate having a surface area between 1 $m^2/g$ and about 20 $m^2/g$, wherein the support material and the diluent are chemically different,
   wherein the support material is selected from the group consisting of alumina, silica, magnesia, kieselguhr, fuller's earth, clays, porous rare earth halides and oxyhalides, and combinations thereof, and wherein the surface area of the support material is between about 5 $m^2/g$ and about 450 $m^2/g$.

2. The oxychlorination catalyst composition of claim 1, wherein the average particle size of the diluent is between about 25% and about 200% of the average particle size of the oxychlorination catalyst.

3. The oxychlorination catalyst composition of claim 1, wherein the % attrition of the diluent is between about 50% and about 150% of the % attrition of the oxychlorination catalyst.

4. The oxychlorination catalyst composition of claim 1, wherein the alumina silicate comprises meta-kaolin, kaolin calcined through its characteristic exotherm, or a combination thereof.

5. The oxychlorination catalyst composition of claim 4, wherein the alumina silicate is a kaolin calcined through its characteristic exotherm.

6. The oxychlorination catalyst composition of claim 5, wherein the calcined kaolin is in the form of microspheres.

7. An oxychlorination catalyst composition comprising:
   (a) a catalytically effective amount of an oxychlorination catalyst having a surface area between about 50 $m^2/g$ and about 250 $m^2/g$ wherein the oxychlorination catalyst comprises a support material having distributed thereon an active salt composition; and
   (b) a diluent having a surface area between about 1 $m^2/g$ and about 20 $m^2/g$, wherein the support material and the diluent are different chemically and the average particle size of the oxychlorination catalyst is from about 5 microns to about 300 microns and the average particle size of the diluent is from about 5 microns to about 300 microns.

8. The oxychlorination catalyst composition of claim 7, wherein the oxychlorination catalyst comprises an active salt composition comprising a copper salt.

9. The oxychlorination catalyst composition of claim 7, wherein the active salt composition comprises from about 2% to about 12% by weight of copper, from about 0.2% to about 3% by weight of an alkali metal, from about 0.1% to about 14% by weight of a rare earth metal, and from about 0.05% by weight to about 6% by weight of an alkaline metal, all weight percents based upon the total weight of the oxychlorination catalyst.

10. The oxychlorination catalyst composition of claim 7, wherein the diluent is a dehydroxylated, dehydrated or calcined alumina silicate.

11. The oxychlorination catalyst composition of claim 7, wherein the average particle size of the diluent is between about 75% and about 125% of the average particle size of the oxychlorination catalyst.

12. The oxychlorination catalyst composition of claim 11, wherein the tamped bulk density of the diluent is about 25% to about 200% of the tamped bulk density of the oxychlorination catalyst.

13. The oxychlorination catalyst composition of claim 7, wherein the % attrition of the diluent is between about 50% and about 150% of the % attrition of the oxychlorination catalyst.

14. The oxychlorination catalyst composition of claim 1, wherein the surface area of the diluent particles is from about 0.1 $m^2/g$ to about 25 $m^2/g$.

15. The oxychlorination catalyst composition of claim 1, wherein the surface area of the diluent particles is from about 1 $m^2/g$ to about 20 $m^2/g$.

16. The oxychlorination catalyst composition of claim 1, wherein the surface area of the diluent particles is from about 3 $m^2/g$ to about 16 $m^2/g$.

17. The oxychlorination catalyst composition of claim 1, wherein the active salt composition comprises a copper salt.

18. The oxychlorination catalyst composition of claim 1, wherein the active salt composition comprises from about 2% to about 12% by weight of copper, from about 0.2% to about 3% by weight of an alkali metal, from about 0.1% to about 14% by weight of a rare earth metal, and from about 0.05% by weight to about 6% by weight of an alkaline metal, all weight percents based upon the total weight of the oxychlorination catalyst.

19. The oxychlorination catalyst composition of claim 18, wherein the support material and the diluent are different chemically.

20. The oxychlorination catalyst composition of claim 18, wherein the support material is alumina having a surface area greater than 50 $m^2/g$.

21. The oxychlorination catalyst composition of claim 1, wherein the oxychlorination catalyst has a surface area from about 25 $m^2/g$ to about 300 $m^2/g$.

22. The oxychlorination catalyst composition of claim 1, wherein the oxychlorination catalyst has a surface area from about 50 $m^2/g$ to about 200 $m^2/g$.

23. The oxychlorination catalyst composition of claim 1, wherein the oxychlorination catalyst has a surface area from about 70 $m^2/g$ to about 150 $m^2/g$.

24. The oxychlorination catalyst composition of claim 1, wherein the oxychlorination catalyst composition comprises from about 10 to about 90 percent by weight of the oxychlorination catalyst and from about 90 to about 10 percent by weight of the diluent.

* * * * *